United States Patent [19]
Kugo et al.

[11] Patent Number: 5,507,766
[45] Date of Patent: Apr. 16, 1996

[54] VASCULAR DILATATION INSTRUMENT AND CATHETER

[75] Inventors: Takahiro Kugo; Akihiko Umeno, both of Fujinomiya; Kiyoshi Yamauchi, Sendai; Hiroshi Ishikawa, Sendai; Tadashi Seto, Sendai, all of Japan

[73] Assignees: Terumo Kabushiki Kaisha, Tokyo; Tokin Corporation, Sendai, both of Japan

[21] Appl. No.: 186,563

[22] Filed: Jan. 26, 1994

[30] Foreign Application Priority Data

Jan. 26, 1993 [JP] Japan .................................. 5-031473
Dec. 28, 1993 [JP] Japan .................................. 5-352876

[51] Int. Cl.$^6$ ............................ A61M 29/06; A61B 17/58
[52] U.S. Cl. ................................................ 606/194; 606/95
[58] Field of Search ................................ 606/194, 192, 606/191, 193, 95–96; 604/101, 27, 40, 43, 96; 128/656–658

[56] References Cited

U.S. PATENT DOCUMENTS

| | | | |
|---|---|---|---|
| 4,323,071 | 4/1982 | Simpson et al. | 128/343 |
| 4,573,470 | 3/1986 | Samson et al. | 128/344 |
| 4,840,622 | 6/1989 | Hardy | 604/264 |
| 4,969,890 | 11/1990 | Sugita et al. | 606/192 |
| 4,998,923 | 3/1991 | Samson et al. | 606/194 |
| 5,035,694 | 7/1991 | Kasprzyk et al. | 606/192 X |
| 5,089,005 | 2/1992 | Harada | 606/194 |
| 5,106,363 | 4/1992 | Nobuyoshi et al. | 606/194 X |
| 5,147,370 | 9/1992 | McNamara et al. | 606/194 X |
| 5,180,376 | 1/1993 | Fischell | 604/282 |
| 5,242,396 | 9/1993 | Evard | 606/194 X |
| 5,250,069 | 10/1993 | Nobuyoshi et al. | 606/192 |
| 5,279,562 | 1/1994 | Sirhan et al. | 604/96 |
| 5,290,230 | 3/1994 | Ainsworth et al. | 604/96 |
| 5,312,340 | 5/1994 | Keith | 604/96 |
| 5,346,505 | 9/1994 | Leopold | 606/194 |
| 5,348,537 | 9/1994 | Wiesner et al. | 604/96 |

FOREIGN PATENT DOCUMENTS

| | | |
|---|---|---|
| 0279959 | 8/1988 | European Pat. Off. . |
| 0374859A1 | 6/1990 | European Pat. Off. . |
| 0437795A1 | 7/1991 | European Pat. Off. . |
| 4104092A1 | 8/1991 | Germany . |
| WO89/08473 | 9/1989 | WIPO . |

*Primary Examiner*—Stephen C. Pellegrino
*Assistant Examiner*—Nancy Mulcare
*Attorney, Agent, or Firm*—Burns, Doane, Swecker & Mathis

[57] ABSTRACT

A vascular dilatation instrument 1 includes an outer tube 2, an inner tube 5 extending through the outer tube 2, and an inflatable member 3 having one end attached to the inner tube 5 and another end attached to the outer tube 2. The outer tube 2 includes a superelastic or pseudoelastic metal tube 2b and a synthetic resin tube 2a covering the metal tube, the metal tube 2b having a distal zone provided with a slit or perforations 2e so that the distal zone is more flexible and deformable than the remainder of the metal tube. Also provided is a catheter 100 comprising a main body section which includes a superelastic metal tube 101 and a synthetic resin layer 104 covering the metal tube, the metal tube 101 having a distal zone provided with a slit or perforations 106 so that the distal zone is more flexible and deformable than the remainder of the metal tube.

31 Claims, 25 Drawing Sheets

VASCULAR DILATATION INSTRUMENT AND CATHETER

BACKGROUND OF THE INVENTION

1. Field of the Invention

This invention relates to a vascular dilatation instrument for use in curing a stricture or stenosis portion inside a blood vessel by dilating the stricture for improving blood flow to the peripheral side of the stricture. It also relates to a catheter intended to insert into fine blood vessels, for example, brain and heart vessels for curing and inspection purposes.

2. Prior Art

For curing a stenosed vessel by arterial sclerosis or the like, percutaneous transluminal coronary angioplasty (PTCA) has heretofore been practiced in the art wherein a catheter having a dilator at its distal end is inserted into the vessel until it reaches the stenosis and the dilator is inflated to dilate the stenosis for improving blood flow to the peripheral side thereof.

Known catheters with a dilator include those of the over-the-wire type wherein a guide wire is movable back and forth within a catheter as typified by that disclosed in U.S. Pat. No. 4,323,071 and those of time on-the-wire type wherein a catheter is fixed to a guide wire as typified by that disclosed in U.S. Pat. No. 4,573,470.

The demand for introducing vascular dilatation instruments into finer blood vessels is increasing year by year. There is a need for a vascular dilatation instrument which can be introduced into a finer or more peripheral blood vessel.

Currently available are vascular dilatation instruments and catheters of the over-the-wire and on-the-wire types both using a superelastic metal tube. These instruments are fully effective in transmitting translational and torsional forces (pushing force and torque) from the proximal end to the distal end of the instrument.

However, vascular dilatation instruments of the over-the-wire the-wire type can be folded at an angle where the superelastic metal tube terminates, that is, near the distal end of the superelastic metal tube. Vascular dilatation instruments of the on-the-wire type suffer from a loss of flexibility at their distal portion because the tubular member is entirely formed of a superelastic metal tube. Although attempts were made to render the distal portion flexible, none of them succeeded in providing flexibility as available with resins probably because of the superelastic metal tube.

Therefore, an object of the present invention is to provide a novel and improved vascular dilatation instrument which is effective for transmitting translational and torsional forces, which has a fully flexible distal portion and a highly stiff body portion, which prevents angular bending due to a change of physical properties at the interface between the stiff body portion and the flexible distal portion, and which is convenient to manipulate.

Conventional catheters to be inserted into blood vessels, for example, angiographic catheters and catheters for administering medicament into vessels are made of relatively flexible thermoplastic resins. One recent design includes a rigidity imparting member in the form of a metal wire (often a stainless steel wire) disposed around the catheter for preventing angular bending or collapse of the catheter and improving torque transmission while maintaining a flexible state.

With the recent advance of medical technology, it is now required to introduce a catheter into such a site as a smaller diameter vessel as found in the heart and brain. Diseases in cerebral vessels include aneurysm, arteriovenous malformation (AVM), and dual AVM. For inspection and treatment of such diseases, it is desired to have a catheter which can be inserted into a finer blood vessel or more peripheral blood vessel site.

However, the above-mentioned catheter has a main body portion made of a synthetic resin tube, which must have a certain wall thickness. It is thus inevitable that the outer diameter is increased by the extra wall thickness. Since the blood vessel into which the catheter can be introduced is restricted by its outer diameter, the catheter could only be introduced into a blood vessel sufficiently larger than the outer diameter of the catheter. If the catheter is made of a more rigid material, then the catheter as a whole is harder, leaving problems including the risk of the distal end causing damage to the vessel wall upon insertion and difficulty of insertion.

Therefore, another object of the present invention is to provide a novel and improved catheter which is reduced in wall thickness and hence, outer diameter and includes a fully flexible distal portion.

SUMMARY OF THE INVENTION

According to a first aspect of the present invention, there is provided a vascular dilatation instrument comprising an inner tube defining a first lumen extending between an open distal end and a proximal portion. An outer tube is disposed coaxially around the inner tube, has a distal end retracted a predetermined distance from the distal end of the inner tube and a proximal portion and defines a second lumen with the outside surface of the inner tube. An inflatable member or dilator has one end attached to the inner tube and another end attached to the outer tube and defines an interior space in fluid communication with the second lumen in the vicinity of the other end. A first opening is disposed in the proximal portion of the inner tube in communication with the first lumen, and a second opening disposed in the proximal portion of the outer tube in fluid communication with the second lumen. At least one of the inner tube and the outer tube includes a main body section made of a superelastic or pseudoelastic metal tube covered with a synthetic resin and a distal section made of a synthetic resin. The superelastic metal tube includes a deformable distal zone which is more flexible than the remainder of the metal tube.

According to a second aspect of the present invention, there is provided a vascular dilatation instrument comprising a tubular member having a lumen therethrough and an opening in fluid communication with the lumen, a leading head, and an inflatable member or dilator having one end attached to the tubular member and another end attached to the leading head and defining an interior space in fluid communication with the lumen through the opening. The tubular member includes a main body portion made of a superelastic or pseudoelastic metal tube covered with a synthetic resin and a distal portion made of a synthetic resin. The superelastic metal tube includes a deformable distal zone which is more flexible than the remainder.

According to a third aspect of the present invention, there is provided a catheter comprising a main body section including a superelastic or pseudoelastic metal tube and a synthetic resin layer covering the metal tube, and a distal section made of a synthetic resin. The superelastic metal tube includes a deformable distal zone which is provided with a slit or a plurality of perforations.

DETAILED DESCRIPTION OF THE INVENTION

Figure 1:
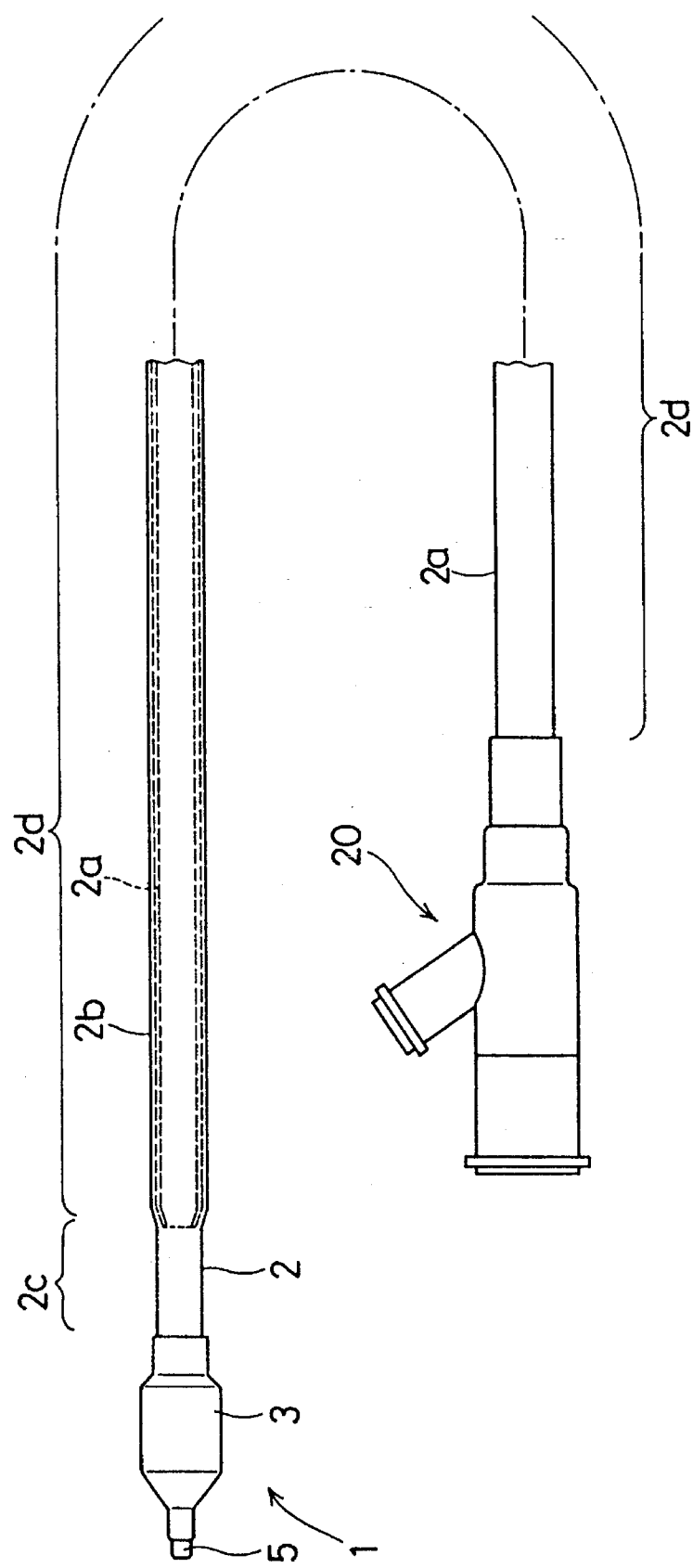
FIG. 1 is an overall, partially omitted, schematic view of a vascular dilatation instrument according to one embodiment of the invention.

The vascular dilatation instrument of the present invention is described with reference to various embodiments shown in FIGS. 1 through 23.

In the first aspect, the vascular dilatation instrument is defined as comprising an inner tube 5 defining a first lumen 4 extending between an open distal end and a proximal portion; an outer tube 2 disposed coaxially around the inner tube 5, having a distal end retracted a predetermined distance from the distal end of the inner tube and a proximal portion, and defining a second lumen 6 with the outside surface of the inner tube; an inflatable member or dilator 3 having one end attached to the inner tube 5 and another end attached to the outer tube 2 and defining an interior space in fluid communication with the second lumen 6 in the vicinity of the other end; a first opening 9 disposed in the proximal portion of the inner tube 5 in communication with the first lumen 4; and a second opening 11 disposed in the proximal portion of the outer tube 2 in fluid communication with the second lumen 6. At least one of the inner tube 5 and the outer tube 2 includes a main body section based on a superelasLic metal tube and a distal section made of a synthetic resin. The superelastic metal tube includes a deformable distal zone which is more flexible than the remainder.

Referring to FIGS. 1 to 6, there is illustrated a vascular dilatation instrument according to one embodiment of the invention. The instrument generally designated at 1 comprises a main body including an inner tube 5, an outer tube 2, and a dilator 3 and a branch hub or adapter 20.

The outer tube 2 of the vascular dilatation instrument 1 includes a main body portion 2d including a superelastic metal tube 2b and a distal portion 2c made of a synthetic resin. The superelastic metal tube 2b includes a distal zone which forms a junction between the main body portion 2d and the distal portion 2c and is more flexible than the remainder of the metal tube.

More particularly, the outer tube 2 includes the superelastic metal tube 2b and a synthetic resin tube 2a enclosing and covering the surface or the metal tube. The synthetic resin tube 2a protrudes beyond the distal end of the superelastic metal tube 2b where it forms the distal portion 2c of the outer tube 2.

Figure 2:
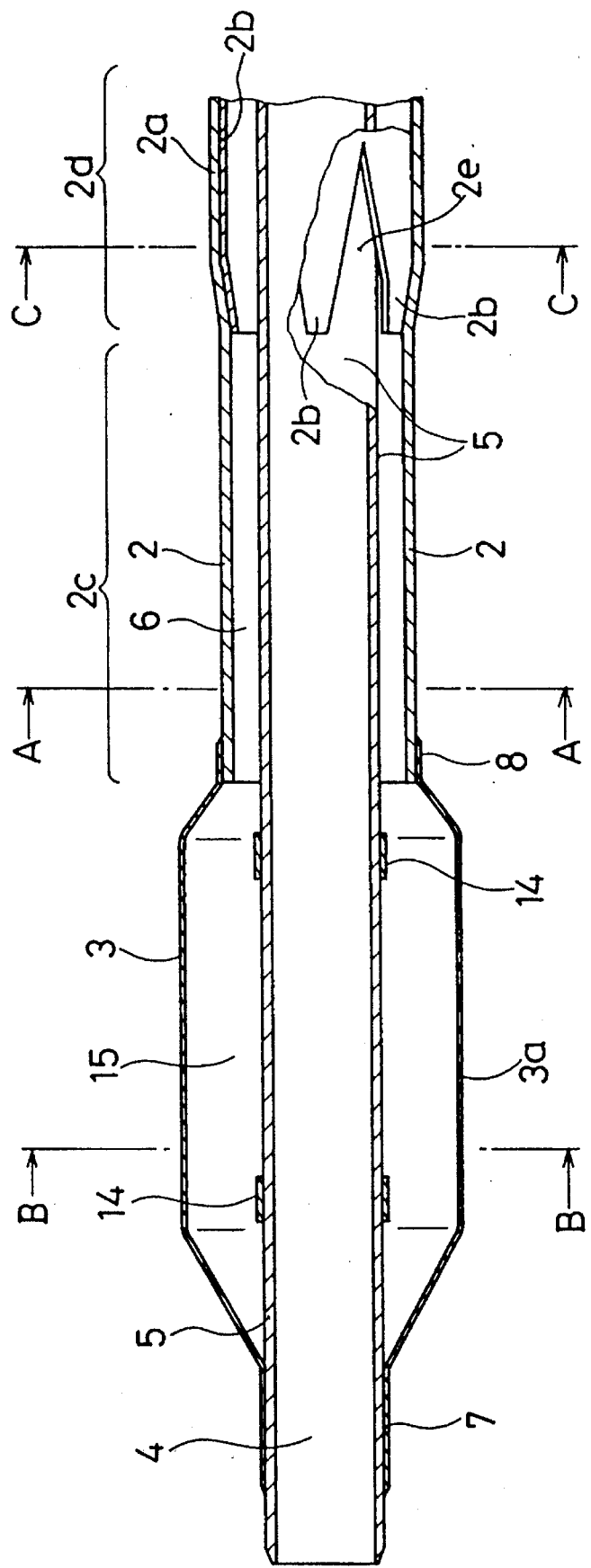
FIG. 2 is an enlarged cross-sectional view of the distal portion of the instrument shown in FIG. 1.
Figure 5:
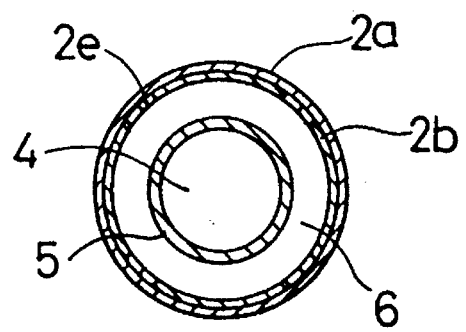
FIG. 5 is a cross section taken along lines C—C in FIG. 2.

As shown in FIG. 2 and FIG. 5 which is a C—C cross section of FIG. 2, the superelastic metal tube 2b includes a distal zone which is provided with slits 2e extending from the distal end (left end in FIG. 2) toward the proximal end. Provision of the slits 2e ensures that the distal zone of the superelastic metal tube 2b is a deformable zone which is more flexible than the remainder. More particularly, the distal zone of the superelastic metal tube 2b is flexible in that its side wall is deformable radially inward or outward. As shown in FIG. 2, each slit 2e is gradually decreased in width from the distal end toward the proximal end of the superelastic metal tube 2b, or differently stated, gradually increased in width toward the distal end. The slit has the maximum width at the distal end of the metal tube 2b. Then as one goes toward the distal end, the superelastic metal tube 2b is more flexible and deformable and the side wall is more deformable radially inward and outward. Preferably two to eight slits 2e are formed at approximately equal intervals. Also preferably, the slits 2e have a maximum width of about 0.05 to 0.5 mm at the distal end (as measured in a circumferential direction) and a length of about 100 to 1,000 mm, especially about 150 to 500 mm (as measured in a longitudinal direction).

In the vascular dilatation instrument 1 of the illustrated embodiment, the superelastic metal tube 2b includes a distal zone which is tapered as shown in FIGS. 1 and 2. More particularly, the side wall defining the distal zone where the slits are formed is bent radially inward. This tapered distal zone can be formed by working the slit distal zone of the metal tube 2b to the configuration shown in FIG. 2. Alternatively, the synthetic resin tube 2a is molded or fitted over the metal tube 2b such that the outer diameter of that portion of the resin tube 2a surrounding the metal tube distal zone is reduced. That is, the metal tube distal zone is deformed radially inward by the resin tube 2a. Then that portion of the resin tube 2a extending forward (to the left in FIG. 2) beyond the metal tube 2b has a smaller diameter than that portion of the resin tube 2a around the metal tube 2b. Since the forward or protruding portion 2c formed solely of the resin tube 2a has a smaller diameter than the main body portion including the metal tube 2b, it becomes possible to insert the distal portion of the vascular dilatation instrument 1 into a vessel on a more peripheral side. Since the transition between the main body portion 2d and the distal portion 2c of the outer tube 2 (which corresponds to the distal zone of the metal tube 2b) is tapered forward, insertion into a vessel is facilitated.

Since the main body portion 2d of the outer tube 2 has the superelastic metal tube 2b, the vascular dilatation instrument 1 is effective in transmitting translational and torsional forces from the proximal end to the distal end of the instrument, that is, improved in pushability and torque transmission. The distal portion 2c made solely of synthetic resin has sufficient flexibility. The transition between the main body portion 2d and the distal portion 2c of the outer tube 2 (which corresponds to the distal zone of the metal tube 2b) is a more flexible deformable portion and is effective in preventing acute bending at the interface between the relatively stiff main body portion and the relatively flexible distal portion.

Typically the outer tube 2 has an outer diameter of about 0.6 to 2.8 mm, preferably 0.8 to 2.6 mm and an inner diameter of about 0.5 to 2.7 mm, preferably 0.6 to 2.0 mm. The difference between the outer diameter of the inner tube 5 and the inner diameter of the outer tube 2 is about 0.05 to 1.2 mm, preferably 0.1 to 1.2 mm. The outer tube 2 has a wall thickness of about 0.05 to 0.75 mm, preferably 0.07 to 0.3 mm.

The superelastic or pseudoelastic metal tube 2b is preferably made of a superelastic alloy. The superelastic alloys are generally known as shape memory alloys and exert superelasticity at the living body temperature (about 37° C.) or higher. Preferred examples of the superelastic alloy include Ti—Ni binary alloys consisting essentially of 49 to 53 atom % of nickel and the balance of titanium, Cu—Zn binary alloys consisting essentially of 38.5 to 41.5% by weight of zinc and the balance of copper, Cu—Zn—X ternary alloys containing 1 to 10% by weight of X wherein X is Be, Si, Sn, Al or Ga, and Ni—Al binary alloys consisting essentially of 36 to 38 atom % of aluminum and the balance of nickel, with the Ti—Ni alloys being most preferred. Mechanical properties may be properly controlled by replacing part of Ti—Ni alloy by 0.01 to 10.0 atom % of X to form Ti—Ni—X alloys wherein X is Co, Fe, Mn, Cr, V, Al, Nb, W or B or replacing part of Ti—Ni alloy by 0.01 to 30.0 atom % of X to form Ti—Ni—X alloys wherein X is Cu, Pd or Zr and/or selecting the conditions of cold working and/or final heat treatment. By the term "superelasticity" it is meant that when an alloy is deformed (bent, stretched or compressed) at service temperature to the extent where conventional metals undergo plastic deformation and then released from deformation, the alloy resumes the original shape without a need for heating.

Typically the superelastic metal tube 2b has an outer diameter of about 0.6 to 2.0 mm, preferably 0.8 to 1.6 mm, a wall thickness of about 50 to 200 μm, preferably 80 to 150 μm, a length of about 500 to 4,000 mm, preferably 1,000 to 3,000 mm, a buckling strength (yield stress under load) of about 5 to 200 kg/mm$^2$, preferably 8 to 150 kg/mm$^2$ at 22° C., and a restoring stress (yield stress upon unloading) of about 3 to 180 kg/mm$^2$, preferably 5 to 130 kg/mm$^2$ at 22° C.

Slits or perforations are formed in the superelastic metal tube by any of conventional techniques including laser machining (e.g., YAG laser), electric discharge machining, chemical etching, machining, and combinations thereof.

For the synthetic resin tube 2a of the outer tube 2, materials having a certain degree of flexibility are used, for example, thermoplastic resins such as polyolefins (e.g., polyethylene, polypropylene, and ethylene-propylene copolymers), polyvinyl chloride, ethylene-vinyl acetate copolymers, polyamide elastomers, and polyurethane, and silicone rubber. Preferred are the thermoplastic resins, especially polyolefins. That portion of the synthetic resin tube 2a surrounding and covering the superelastic metal tube 2b preferably has a wall thickness of about 5 to 300 μm, more preferably 10 to 200 μm.

The outside surface of the outer tube 2 (more specifically, the outside surface of synthetic resin tube 2a) may be coated with a biocompatible, especially anti-thrombotic, resin. Preferred anti-thrombotic resins are poly(hydroxyethyl methacrylate) and hydroxyethyl methacrylate-styrene copolymers (e.g., HEMA-St-HEMA block copolymers).

Although part of the resin material of which the resin tube 2a is made may flow into the slits 2e in the superelastic metal tube 2b, it is preferred that the slits 2e be substantially free of the resin material and empty. In the absence of the resin material flowing into the slits, deformation of the superelastic metal tube 2b is never obstructed.

Alternatively, a heat-shrinkable tube may be used as the synthetic resin tube 2a of the outer tube 2. The heat-shrinkable tube used herein is a tube which has an inner diameter larger than the outer diameter of the superelastic metal tube 2b prior to heating and thus allows the superelastic metal tube to be inserted therethrough, but on heating, shrinks substantially uniformly over its entirety to come in close contact with the outside surface of the metal tube. Such a heat-shrinkable tube is preferably prepared by molding a resin into a tube having an inner diameter equal to or slightly smaller than the outer diameter of the superelastic metal tube, and expanding the tube over its entirety so as to increase its diameter so that upon heating, it may shrink to a diameter equal to or substantially equal to the diameter as molded. The heat-shrinkable tube is made of the material which can be expanded, but shrinks upon heating as mentioned above, for example, polyolefins (e.g., polyethylene, polypropylene, and ethylene-propylene copolymers), ethylene-vinyl acetate copolymers, and polyamide elastomers.

The inner tube 5 has an open distal end and defines the first lumen 4. The first lumen 4 longitudinally extends through the inner tube 5 for allowing a guide wire to be inserted into the tube and is in communication with the first opening 9 disposed in a branch hub 20 to be described later for defining a guide wire port. Typically the inner tube 5 has an outer diameter of 0.40 to 2.50 mm, preferably 0.55 to 2.40 mm and an inner diameter of 0.25 to 2.35 mm, preferably 0.30 to 1.80 mm.

Although the inner tube 5 has an identical diameter throughout its length in FIGS. 1 to 6, the distal portion of the inner tube 5 may be tapered or reduced in diameter toward the distal end because tapering facilitates insertion of the vascular dilatation instrument into a vessel.

For the inner tube 5, materials having a certain degree of flexibility are used, for example, thermoplastic resins such as polyolefins (e.g., polyethylene, polypropylene, and ethylene-propylene copolymers), polyvinyl chloride, ethylene-vinyl acetate copolymers, polyamide elastomers, and polyurethane, and silicone rubber and latex rubber. Preferred are the thermoplastic resins, especially polyolefins.

Figure 3:
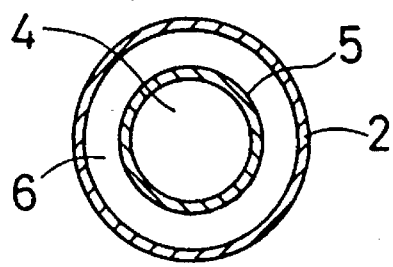
FIG. 3 is a cross section taken along lines A—A in FIG. 2.

The inner tube 5 is inserted through the outer tube 2 until the distal portion of the inner tube 5 protrudes beyond the outer tube 2 as shown in FIG. 2. As best shown in FIG. 2 and FIG. 3 which is a A—A cross section of FIG. 2, the outside surface of the inner tube 5 defines the second lumen 6 with the inside surface of the outer tube 2. The second lumen 6 then longitudinally extends from near the distal portion to the proximal end and has a sufficient volume. The second lumen 6 is in fluid communication on the distal side with the interior space of the inflatable member 3 and on the proximal side with the second opening 11 disposed in the branch hub 20 for defining an injection port for injecting a fluid (for example, vasographic contrast liquid) for inflating the dilator 3.

Figure 4:
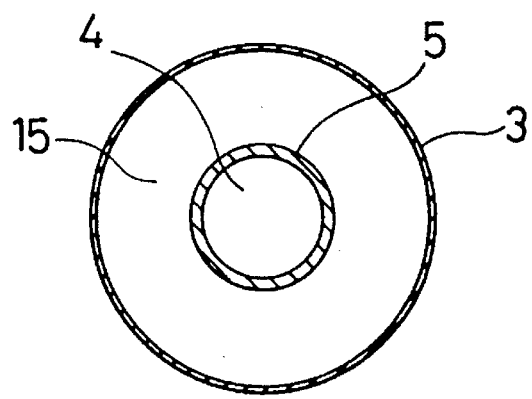
FIG. 4 is a cross section taken along lines B—B in FIG. 2.

The inflatable member or dilator 3 is a contractible or foldable sleeve membrane so that it may be folded flat on the outside surface of the inner tube 5 in its deflated state. The inflatable member 3 includes a substantially cylindrical portion 3a having an approximately uniform diameter at least a part of which is substantially cylindrical, when inflated, for dilating the stricture in a blood vessel and is foldable in close contact with the inner tube 5 when deflated. The cylindrical portion 3a need not be completely cylindrical, but may be polygonal. The inflatable member 3 has one end 8 which is secured in a liquid tight manner to the distal end of the outer tube 2 by adhesion, fusion welding or the like and another end 7 which is similarly secured in a liquid tight manner to the distal portion of the inner tube 5. As shown in FIG. 4 which is a B—B cross section of FIG. 2, the inflatable member 3 defines an interior space 15 between its inside surface and the outside surface of the inner tube 5 when inflated. The inflation interior space 15 is in fluid communication with the second lumen 6 at the one end 8 of the inflatable member 3 over its entire circumference. Since the inflatable member 3 at one end 8 is in communication with the second lumen 6 having a relative large volume, it is easy to inject a fluid into the inflatable member 3 interior space through the second lumen 6.

For the inflatable member 3, materials having flexibility and elasticity are used, for example, thermoplastic resins such as polyolefins (e.g., polyethylene, polypropylene, and ethylene-propylene copolymers), polyvinyl chloride, ethylene-vinyl acetate copolymers, crosslinked ethylene-vinyl acetate copolymers, polyurethane, polyesters (e.g., polyethylene terephthalate), and polyamide elastomers, and silicone rubber and latex rubber. Preferred are the thermoplastic resins, especially crosslinked ethylene-vinyl acetate copolymers.

The inflatable member 3 includes tapered transition portions between the cylindrical portion 3a and the opposed ends 7 and 8 attached to the inner and outer tubes 5 and 2, respectively. With respect to the dimensions of the inflatable member 3, the cylindrical portion 3a when inflated preferably has an outer diameter of about 1.5 to 35.0 mm, more preferably 2.0 to 30.0 mm and a length of about 10.0 to 80.0 mm, more preferably 15.0 to 75.0 mm. The inflatable member 3 preferably has an overall length of about 15 to 120 mm, more preferably 20 to 100 mm.

Markers 14 are preferably provided on the outside surface of the inner tube 5. More particularly, as shown in FIG. 2, the markers 14 are disposed at a position rearward of and near the attachment between the dilator 3 and the inner tube 5 and a position forward of and near the attachment between the dilator 3 and the outer tube 2, that is, in alignment with the opposed ends of the cylindrical portion 3a. The markers 14 are made of a radiopaque material, for example, gold, platinum or alloys thereof. The provision of the markers 14 ensures easy location of the dilator 3 under radiological imaging. The markers 14 are preferably formed by fastening a ring of the above-mentioned metal around the inner tube 5 as by crimping whereby their clear radiographic images are always obtained.

In order to facilitate insertion of the vascular dilatation instrument 1 of the invention into a blood vessel or a guide catheter, the outer tube 2 and dilator 3 on their outside surface are preferably treated so that the outside surface may exhibit lubricity when contacted with blood or body fluid. Such treatments include coating and fixation of hydrophilic polymers such as poly(2-hydroxyethyl methacrylate), poly-(hydroxyethyl acrylate), hydroxypropyl cellulose, methyl vinyl ether-maleic anhydride copolymers, polyethylene glycol, polyacrylamide, and polyvinyl pyrrolidone.

Figure 6:
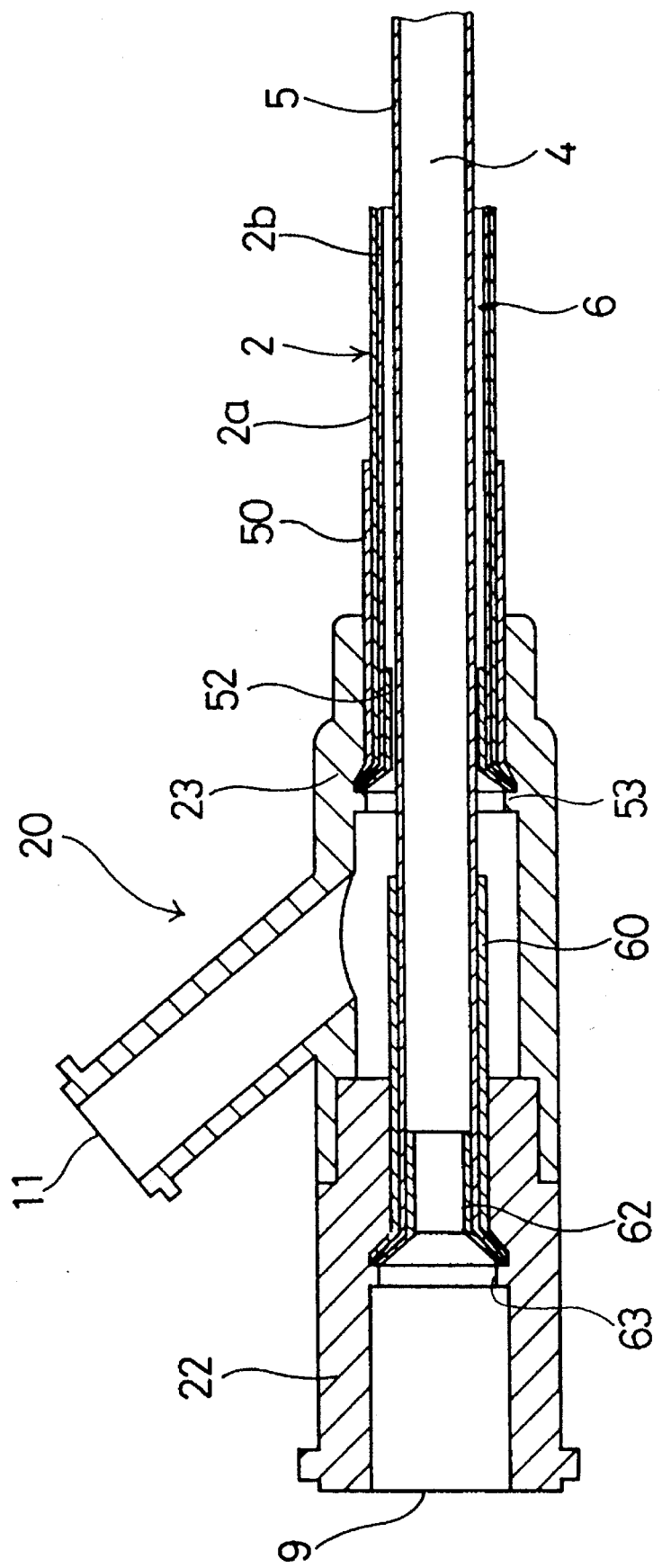
FIG. 6 is an enlarged cross-sectional view of the proximal portion of the instrument shown in FIG. 1.

As shown in FIGS. 1 and 6, the branch hub or adapter 20 is attached to the proximal end of the instrument. The branch hub 20 includes fixedly mated inner and outer hub segments 22 and 23. The inner hub segment 22 is fixedly connected to the inner tube 5 and has the first opening 9 in communication with the first lumen 4 and forming a guide wire port. The outer hub segment 23 is fixedly connected to the outer tube 2 (which is a composite body of synthetic resin tube 2a and superelastic metal tube 2b) and has the second opening 11 in communication with the second lumen 6 and forming an injection port.

The branch hub 20 is made of thermoplastic resins such as polycarbonates, polyamides, polysulfones, polyarylates, and methacrylate-butylene-styrene copolymers.

The branch hub 20 is configured as shown in FIG. 6 in which the left-hand side is proximal or rear. An anti-flection sleeve 50 is fitted over the outer tube 2a at the proximal end. The sleeve 50 is formed from a heat-shrinkable material and set in place by molding it into a tubular sleeve such that its inner diameter may be slightly smaller than the outer diameter of the outer tube 2 after heat shrinkage, fitting the sleeve over the outer tube 2 from the proximal end, and heating (by blowing hot air) the sleeve for shrinkage fit over the outer tube 2. The anti-flection sleeve 50 is fixedly secured to the outer hub segment 23 by a locking member 52. More particularly, the locking member 52 includes a cylindrical portion having an outer diameter substantially equal to the inner diameter of the outer tube 2 and a flared rear portion. The locking member 52 is inserted into the outer tube 2 until the flared portion abuts the edge of the outer tube 2. Then the outer tube 2 is inserted into a bore of the outer hub segment 23 until the locking member flared portion reaches a recess defined in the bore of the outer hub segment 23 by an annular hump 53. An adhesive may be applied to the outside surface of the sleeve 50 to be in contact with the outer hub segment 23, thereby achieving a firm joint therebetween. Note that the locking member 52 has a larger inside diameter than the inner tube or is a split one. The outer hub segment 23 is preferably made of thermoplastic resins such as polycarbonates, polyamides, polysulfones, polyarylates, and methacrylate-butylene-styrene copolymers.

Another anti-flection sleeve 60 is fitted over the inner tube 5 at the proximal end. The sleeve 60 is formed from a heat-shrinkable material and set in place by molding it into a tubular sleeve such that its inner diameter may be slightly smaller than the outer diameter of the inner tube 5 after heat shrinkage, fitting the sleeve over the inner tube 5 from the proximal end, and heating (by blowing hot air) the sleeve for shrinkage fit over the inner tube 5. The inner tube 5 with anti-flection sleeve 60 is fixedly secured to the inner hub segment 22. This attachment is assisted by a locking member 62. More particularly, the locking member 62 includes a cylindrical portion having an outer diameter substantially equal to the inner diameter of the inner tube 5 and a flared rear portion. The locking member 62 is inserted into the inner tube 5 until the flared portion abuts the edge of the inner tube 5. Then the inner tube 5 is inserted into a bore of the inner hub segment 22 until the locking member flared portion reaches a recess defined in the bore of the inner tube hub 22 by an annular hump 63. An adhesive may be applied to the outside surface of the sleeve 60 to be in contact with the inner hub segment 22, thereby achieving a firm joint therebetween. The inner hub segment 22 is preferably made of thermoplastic resins such as polycarbonates, polyamides, polysulfones, polyarylates, and methacrylate-butylene-styrene copolymers.

The inner and outer hub segments 22 and 23 are engaged as shown in FIG. 6. This engagement is achieved by attaching the outer hub segment 23 to the proximal end of the outer tube 2, attaching the inner hub segment 22 to the proximal end of the inner tube 5, inserting the inner tube 5 from its distal end into the bore of the outer hub segment 23 at the proximal end until the inner hub segment 22 contacts the outer hub segment 23, and tightly coupling the inner and outer hub segments 22 and 23. At this point, an adhesive may be applied to the interface between the inner and outer hub segments 22 and 23 to form a firm joint.

Instead of the branch hub 20, tubing sections each having a port member defining an opening at a proximal end may be liquid-tightly attached to the first and second lumens, respectively.

Figure 7:
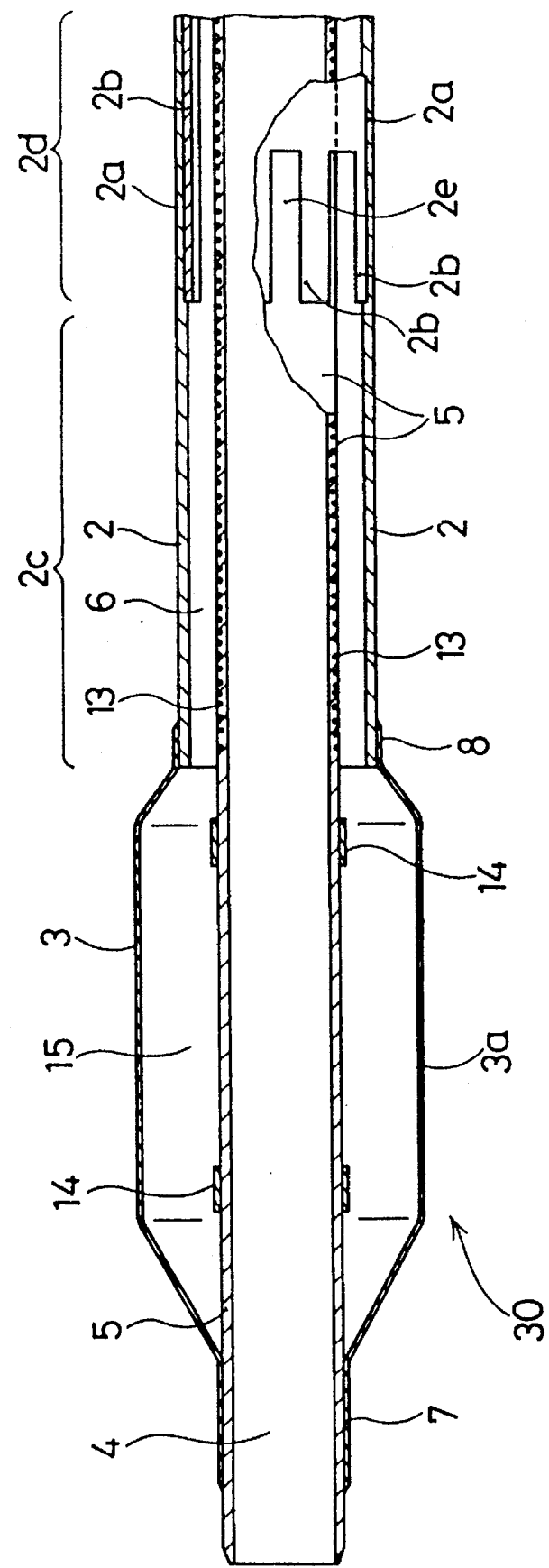
FIGS. 7, 8, 9, 10, 11 and 12 are enlarged cross-sectional views of modified distal portions of vascular dilatation instruments according to the invention.

The structure of the outer tube 2 is not limited to that shown in FIG. 2. Another exemplary structure of the outer tube is shown in FIG. 7. Unlike the embodiment of FIG. 2, a vascular dilatation instrument 30 of this embodiment includes an outer tube 2 having a substantially identical outer diameter over its entirety. The outer tube 2 includes a superelastic metal tube 2b having slits 2e formed at a distal zone thereof as in FIG. 2, but having an identical width while extending parallel from the distal end toward the proximal side. Preferably two to eight slits 2e are formed at substantially equal intervals. The slits 2e preferably have a circumferential width of about 0.05 to 0.5 mm and a length of about 50 to 200 mm.

In the vascular dilatation instrument 30 of this embodiment, the inner tube 5 further includes a rigidity imparting member or reinforcement 13 which is effective for preventing flection of the instrument main body at the distal portion and enhancing the torque property of the instrument main body. The reinforcement 13 preferably extends from the proximal end of the inner tube 5 to near the distal end of the outer tube 2. If desired, the reinforcement 13 extends throughout the length of the inner tube 5.

The reinforcement 13 is preferably in the form of a network reinforcement. The network reinforcement is preferably formed of a braided wire of stainless steel, elastic metal, superelastic or pseudoelastic alloy, shape memory alloy or the like, having a diameter of about 0.01 to 0.2 mm, especially 0.03 to 0.1 mm. By wrapping such a metal wire around the inner tube 5, a reinforcement is formed. More preferably, a reinforced inner tube is prepared by molding an inner tube from a thermoplastic resin, wrapping a metal wire around the inner tube, and passing the tube through a heating die (while externally heating the tube) for thereby burying the wire in the inner tube wall.

Alternatively, the reinforcement may be formed by wrapping around the inner tube 5 a braided strand of synthetic filaments such as polyamide, polyester and polypropylene filaments. It is also possible that not only the inner tube, but also the outer tube be provided with such reinforcement.

Figure 8:
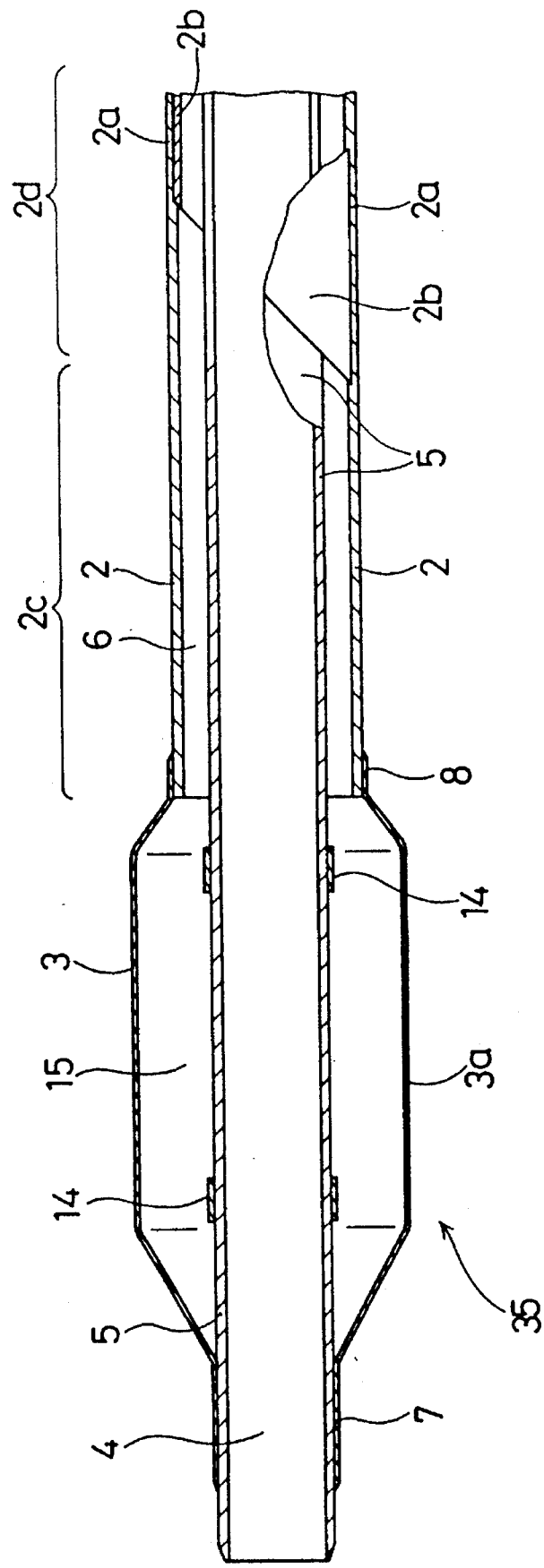

A further exemplary structure of the outer tube is shown in FIG. 8. Unlike the embodiment of FIG. 2, a vascular dilatation instrument 35 of this embodiment includes an outer tube 2 having a substantially identical outer diameter over its entirety. The outer tube 2 includes a superelastic metal tube 2b. The metal tube 2b is cut at an angle with respect to its axis. That is, the metal tube 2b has a beveled distal zone which is more flexible and deformable than the remainder. The cutting angle is preferably from about 5° to 45°.

Figure 9:
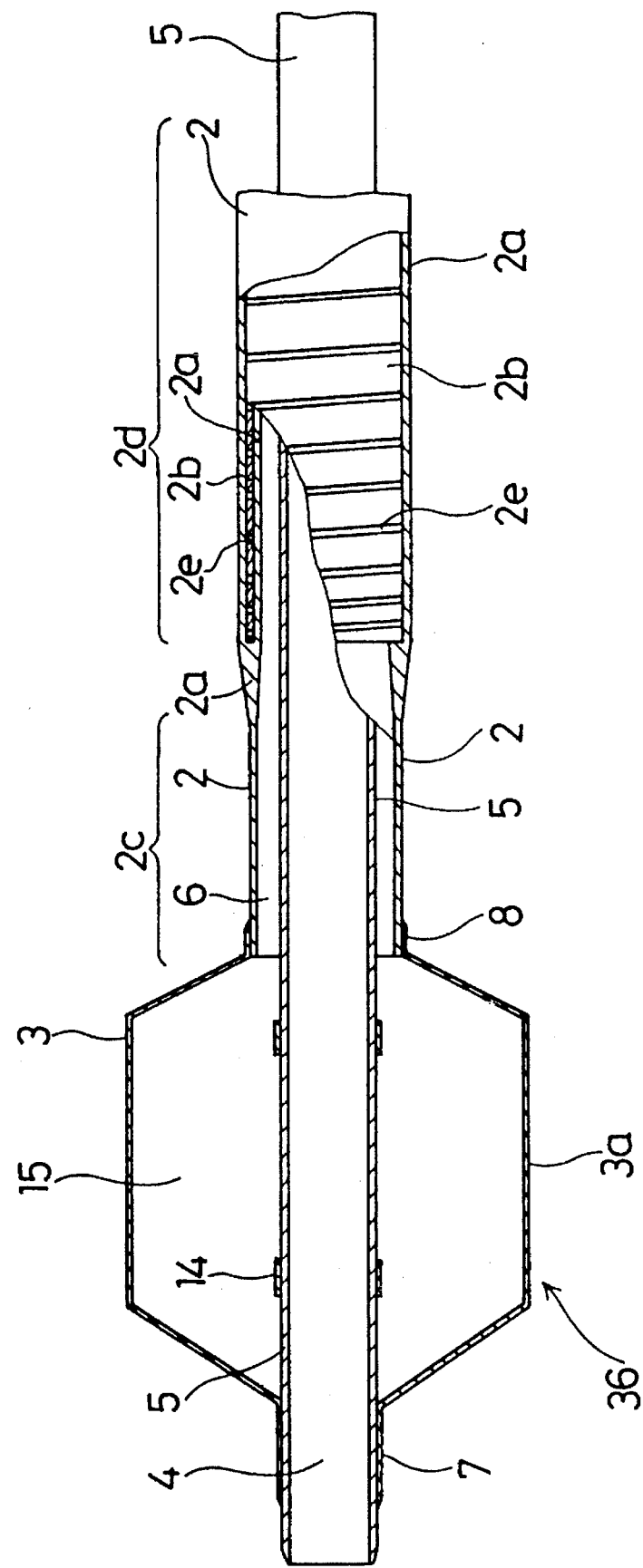

FIG. 9 illustrates a vascular dilatation instrument according to a further embodiment of the invention.

The basic construction of this embodiment is the same as that shown in FIGS. 1 to 6 and like parts are designated by the same numerals as in FIGS. 1 to 6. The difference is the shape of slits in the superelastic metal tube of the outer tube. More particularly, the vascular dilatation instrument 36 of this embodiment includes an outer tube 2 which includes a synthetic resin tube 2a and a superelastic metal tube 2b having a distal zone where a spiral slit 2e is formed. The provision of spiral slit 2e makes the distal zone of the metal tube 2b more flexible and bendable than the remainder. The flexibile distal zone of the metal tube 2b is effective for reducing the difference in physical properties between the superelastic metal tube 2b and the synthetic resin tube 2a for providing a smoother transition, thereby preventing separation and differential motion therebetween. The instrument is more smooth and convenient to manipulate. In the vascular dilatation instrument 36 of this embodiment, the synthetic resin tube 2a is provided not only on the outside surface, but also on the inside surface of superelastic metal tube 2b. Although resin coverage only on the metal tube outside surface is satisfactory, double coverage prevents the risk of the slit edge (or spiral turns) of the metal tube causing damage to the inner tube.

The spiral silt 2e in the superelastic metal tube 2b has a width as measured in an axial direction of the tube. The slit width is not fixed since it is determined in consideration of the outer diameter of the outer tube or the like. The slit width is preferably 0.1 to 1.5 mm, more preferably 0.5 to 1.0 mm. In other words, the slit width is preferably about ⅙ to ⅔, more preferably ⅓ to ½ of the outer diameter of the metal tube. Within this range, the distal portion of the metal tube is fully flexible and not broken during operation. The spiral slit 2e has a pitch between adjacent turns. Where the spiral slit 2e has a constant pitch, the pitch is preferably about 0.3 to 2.0 mm, more preferably 0.5 to 1.0 mm because within this range, the metal tube distal zone is fully flexible and not broken during operation. The extent of the distal zone of the metal tube where the slit is formed is determined by taking into account the length of the instrument or the like. Typically the slit is formed in a distal region of the metal tube which extends about 100–1,000 mm, preferably 150–500 mm from the distal edge thereof.

In another example and preferably, the spiral slit 2e is formed at increasing pitches. As shown in FIG. 9, the slit pitch is shorter at the distal end (left-hand side) and longer at the proximal end (right-hand side). Then the superelastic metal tube 2b distal zone becomes more flexible toward its distal end. Such a gradual change of physical properties ensures smoother bending of the metal tube distal zone and easier manipulation of the instrument. Where the slit has a varying pitch, the pitch is preferably about 0.3 to 3.0 mm at the distal end and about 5 to 10 mm at the proximal end, and an intermediate value at an intermediate region. It is also acceptable that the pitch be continuously increased from the distal end to the proximal end. Within this range, the metal tube distal zone is fully flexible and not broken during operation. A single spiral slit is formed in the embodiment of FIG. 9 although two or more slits may be formed.

Figure 10:
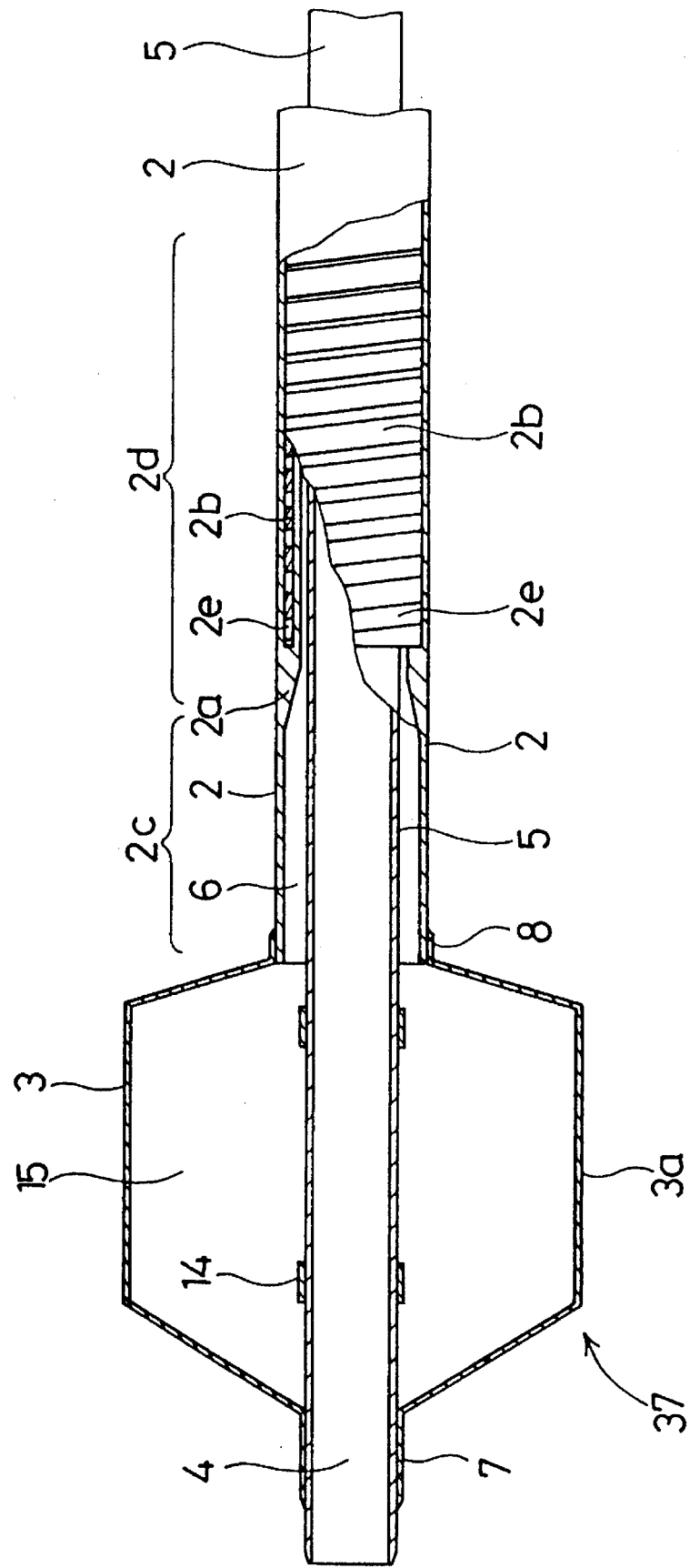

FIG. 10 shows another example of the slit. The vascular dilatation instrument 37 of this embodiment has the same basic construction as the embodiments of FIGS. 1 to 6 and FIG. 9 and like parts are designated by the same numerals. The difference of the instrument 37 of this embodiment from the instruments of the previous embodiments resides in the configuration of the slit 2e in the superelastic metal tube 2b of the outer tube 2.

In the vascular dilatation instrument 37, the superelastic metal tube 2b is provided with a spiral slit 2e having a width which is greater at the distal end and smaller at the proximal end of the distal zone. The slit width is reduced from the distal end toward the proximal end. Then the metal tube becomes more flexible toward the distal end, ensuring smoother bending of the metal tube distal zone and easier manipulation of the instrument.

Although the slit width is determined in consideration of the outer diameter of the outer tube or the like, it is preferably about 1.0 to 2.0 mm at the distal end and about 0.1 to 0.5 mm at the proximal end. The slit width is preferably about one-half to twice the outer diameter of the metal tube. Within this range, the metal tube distal zone is fully flexible and not broken during operation. In an intermediate region between the distal end and slit terminus, the slit width may have an intermediate value or be gradually decreased from the distal end to the slit terminus. The pitch of the slit 2e may be fixed or decreased continuously or stepwise from the distal end toward the proximal end. The extent of the distal zone of the metal tube where the slit is formed is determined by taking into account the length of the instrument or the like. Typically the slit is formed in a distal region of the metal tube which extends about 100–1,000 ms, preferably 150–500 mm from the distal edge thereof. A single spiral slit is formed in the embodiment of FIG. 10 although two or more slits may be formed.

Although part of the resin material of which the resin tube 2a is made may flow into the slits 2e in the superelastic metal tube 2b, it is preferred that the slits 2e be substantially free of the resin material and empty. In the absence of the resin material flowing into the slits, deformation of the superelastic metal tube 2b is never obstructed.

Figure 11:
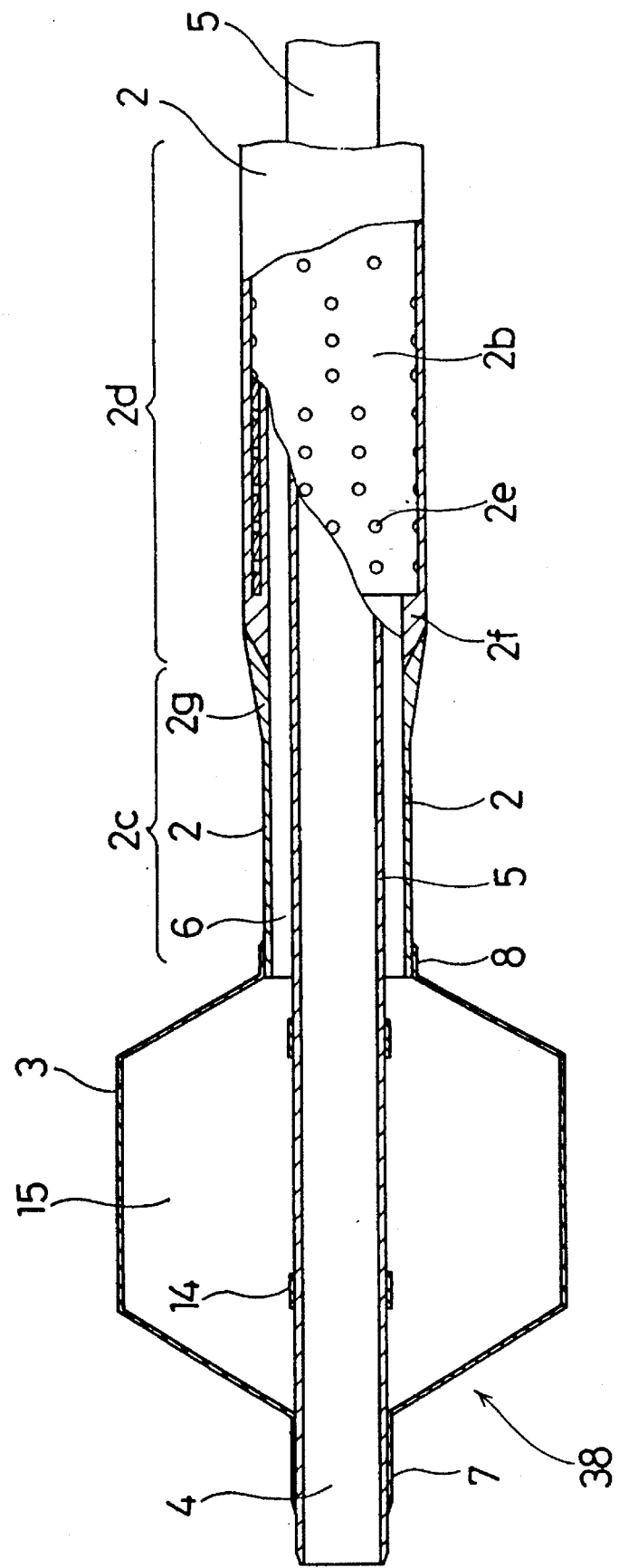

FIG. 11 shows a vascular dilatation instrument according to a further embodiment of the invention. The vascular dilatation instrument 38 of this embodiment has the same basic construction as the embodiment of FIGS. 1 to 6 and like parts are designated by the same numerals. The difference of the instrument 38 of this embodiment from the instrument 1 of the previous embodiment resides in the construction of the outer tube 2. In the instrument 38, the outer tube 2 includes a superelastic metal tube 2b and a synthetic resin tube covering both the outside and inside surfaces of the metal tube 2b which includes a main portion 2f covering the metal tube 2b and a distal portion 2g extending forward from the distal end of the portion 2f. The junction of the main portion 2f to the distal portion 2g is tapered such that the outer diameter is reduced toward the distal end.

The superelastic metal tube 2b in a distal zone is provided with a plurality of perforations 2e so that the metal tube distal zone is flexible and bendable the flexible distal zone of the metal tube 2b reduces the difference in physical properties between the metal tube 2b and the resin tube 2f, thereby preventing separation and differential motion therebetween and enhancing manipulation of the instrument.

The diameter of perforations 2e is not fixed since it is determined in accordance with the number of perforations, the outer diameter of metal tube and the like. Typically the perforations 2e have a diameter of about 0.1 to 0.4 mm, preferably 0.2 to 0.3 mm. The pore diameter is preferably about 1/10 to 1/3 of the outer diameter of the metal tube. Within this range, the metal tube distal zone is fully flexible and not broken during operation. The perforations 2e are preferably spaced a distance of about 0.1 to 0.5 mm. Within this range, the metal tube distal portion is fully flexible and not broken during operation. The extent of the distal zone of the metal tube where the perforations are formed is determined by taking into account the length of the instrument or the like. Typically the perforations are formed in a distal region of the metal tube which extends about 100–1,000 mm, preferably 150–500 mm from the distal edge thereof.

With respect to the shape, the perforations need not be true circle and may be ellipsoidal, for example, oval holes elongated in a circumferential or axial direction of the metal tube or polygonal such as square or pentagonal holes. Each perforation preferably has an area of about 0.007 to 0.13 $mm^2$.

As shown in FIG. 11, more perforations 2e are distributed near the distal end than near the proximal end of the perforated zone. Then the superelastic metal tube 2b becomes more flexible toward the distal end. Such a gradual change of physical properties ensures smoother bending of the metal tube distal zone and more convenient manipulation of the instrument. More specifically, the number of perforations 2e is gradually increased from the proximal end to the distal end of the perforated zone as shown in FIG. 11. Then the superelastic metal tube 2b becomes more flexible toward the distal end, ensuring smoother bending of the metal tube distal zone and easier manipulation of the instrument. Where the perforation distribution is varied in this way, the spacing between perforations is about 0.1 to 0.2 mm at the distal end and about 0.3 to 0.5 mm at the proximal end. In an intermediate region between the distal and proximal ends, the spacing between perforations has an intermediate value or is gradually varied.

Instead of the varying perforation distribution, the diameter or area of perforations may be varied such that the diameter or area is greater near the distal end than near the proximal end of the perforated zone.

Although part of the resin material of which the resin tube portion 2f is made may flow into the perforations 2e in the superelastic metal tube 2b, it is preferred that the perforations 2e be substantially free of the resin material and void. In the absence of the resin material flowing into the perforations, deformation of the metal tube 2b is never obstructed.

Figure 12:
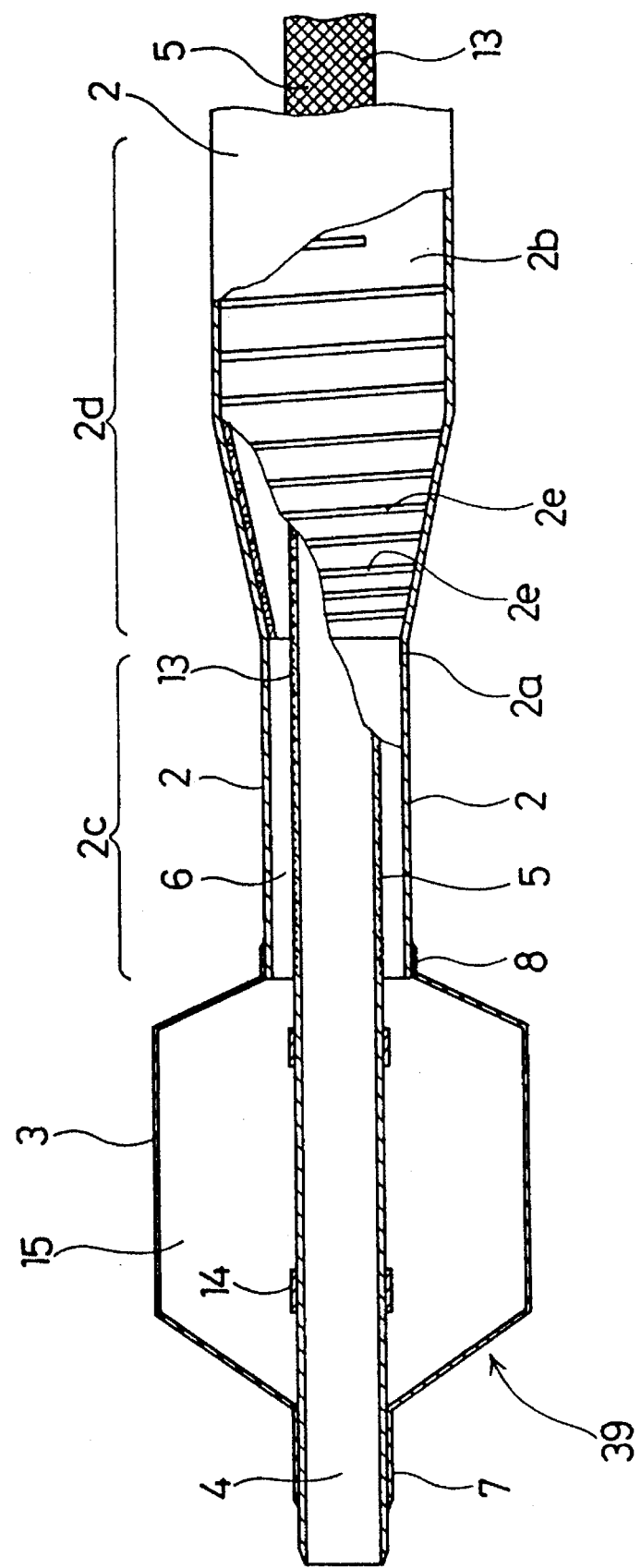

FIG. 12 shows a vascular dilatation instrument according to a further embodiment of the invention. The vascular dilatation instrument 39 of this embodiment has the same basic construction as the embodiment of FIGS. 1 to 6 and like parts are designated by the same numerals. The difference of the instrument 39 of this embodiment from the instrument 1 of the previous embodiment resides in the construction of the outer tube 2. In the instrument 39, the outer tube 2 includes a synthetic resin tube 2a and a superelastic metal tube 2b including a distal zone which is tapered and provided with a spiral slit 2e. The provision of spiral slit 2e allows the metal tube distal zone to flex more softly. The distal zone of the metal tube is tapered such that the outer diameter is reduced toward the distal end. Such a tube can be prepared by forming a tube having a tapered end portion from superelastic metal and machining a slit in the tapered portion. The tube having a tapered end portion can also be prepared by machining a spiral slit in one end portion of a metal tube of a fixed diameter and axially stretching the slit portion. Alternatively, the tube having a tapered end portion can be prepared by machining a spiral slit in one end portion of a metal tube of a fixed diameter and twisting the slit portion such that it is reduced in diameter toward the distal end.

The synthetic resin tube 2a surrounding and covering the outside surface of the superelastic metal tube having a tapered end portion is preferably a heat-shrinkable tube as previously mentioned.

Moreover, the spiral slit 2e is formed at such a pitch that the pitch is shorter at the distal end and longer at the proximal end of the slit region as shown in FIG. 12. Also preferably, the slit pitch is gradually increased from the distal end to the proximal end of the slit region as shown in FIG. 12.

The slit width is not fixed since it is determined in accordance with the outer diameter of the outer tube or the like. The slit width is preferably about 0.1 to 1.5 mm, more preferably 0.5 to 1.0 mm. In other words, the slit width is preferably about 1/6 to 3/2, more preferably about 1/3 to 1/1 of the outer diameter of the metal tube. Within this range, the metal tube distal zone is fully flexible and not broken during operation. Where the spiral slit 2e has a constant pitch, the pitch is preferably about 0.3 to 2.0 mm, more preferably 0.5 to 1.0 mm because within this range, the metal tube distal zone is fully flexible and not broken during operation. Where the slit has a varying pitch, the pitch is preferably about 0.5 to 3.0 mm at the distal end and about 5 to 10 mm at the proximal end of the slit zone and an intermediate value at an intermediate region. It is also acceptable that the pitch be continuously increased from the distal end toward the proximal end. Within this range, the metal tube distal zone is fully flexible and not broken during operation. The extent of the distal portion of the metal tube where the slit is formed is determined by taking into account the length of the instrument or the like. Typically the slit is formed in a distal region of the metal tube which extends 100–1,000 mm, preferably 150–500 mm from the distal edge thereof. A single spiral slit is formed in the embodiment of FIG. 12 although two or more slits may be formed.

Referring to FIGS. 13 through 16, there is illustrated a vascular dilatation instrument according to a further embodiment of the invention. The instrument generally designated at 41 in this embodiment is different from the instrument shown in FIGS. 1 through 6 in that a superelastic metal tube is included in an inner tube.

Figure 13:
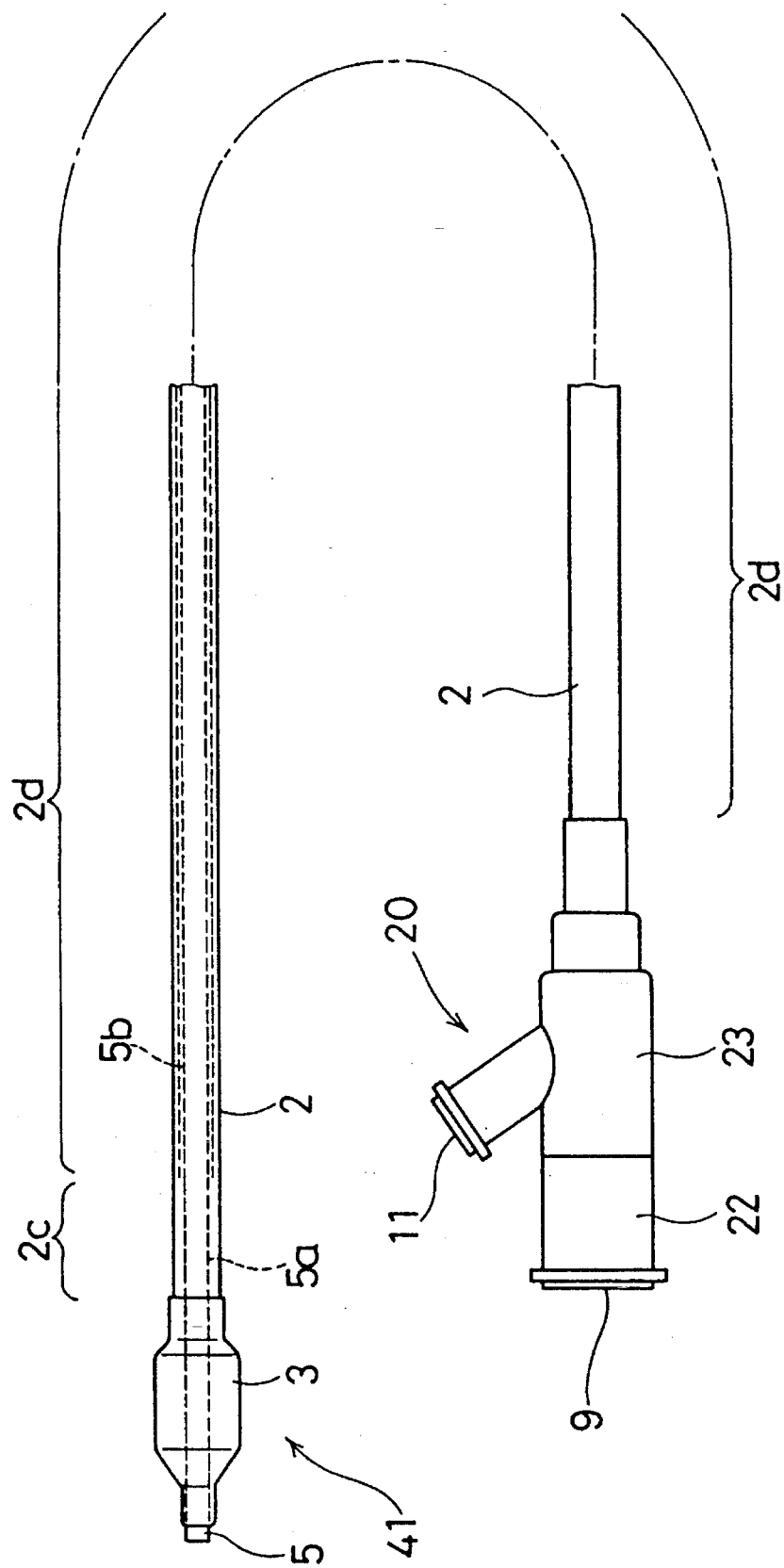
FIG. 13 is an overall, partially omitted, schematic view of a vascular dilatation instrument according to another embodiment of the invention.
Figure 14:
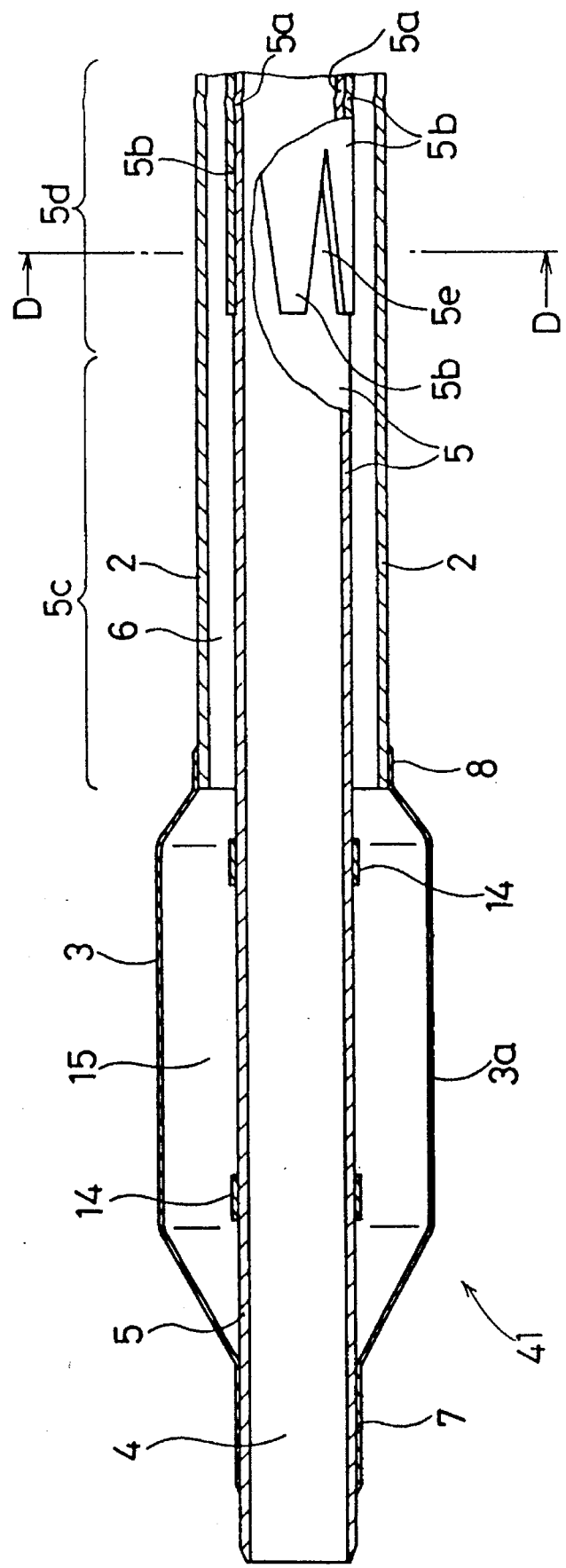
FIG. 14 is an enlarged cross-sectional view of the distal portion of the instrument shown in FIG. 13.
Figure 15:
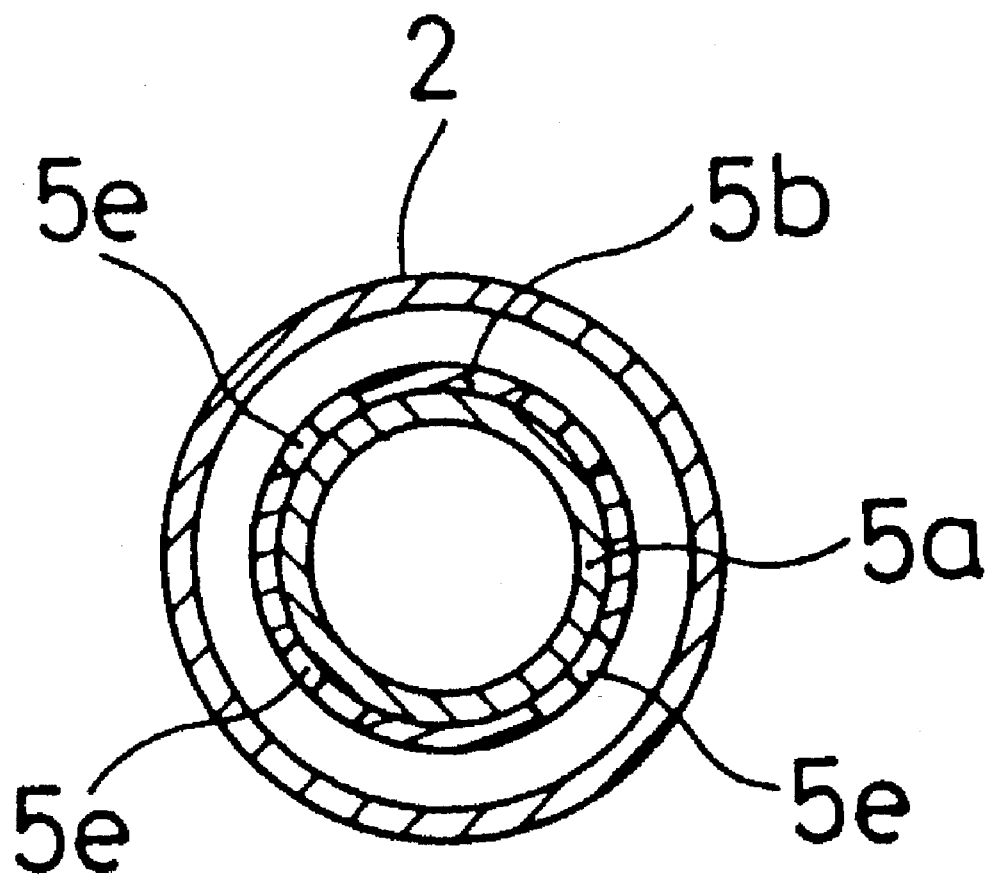
FIG. 15 is a cross section taken along lines D—D in FIG. 14.

In the instrument 41 of this embodiment, as shown in FIG. 13 and FIG. 14 which is an enlarged cross-sectional view of a distal portion of the instrument and FIG. 15 which is a D—D cross section of FIG. 14, the inner tube 5 includes a superelastic metal tube 5b and a synthetic resin tube 5a covering the inside surface of the metal tube. The synthetic resin tube 5a protrudes beyond the distal end of the metal tube 5b to form a distal section 5c. The superelastic metal tube 5b is provided with a plurality of slits 5e extending from the distal end toward the proximal end thereof. The provision of slits 5e makes the distal zone of the metal tube more flexible than the remainder.

As shown in FIG. 14, the triangular slits 5e are gradually decreased in width from the distal end toward the proximal end of the superelastic metal tube 5b, or differently stated, gradually increased in width toward the distal end. The slit has the maximum width at the distal end of the metal tube 5b. Then as one goes toward the distal end, the superelastic metal tube 5b is more flexible and deformable and the side wall is more deformable radially inward and outward. Preferably two to eight slits 5e are formed at approximately equal intervals. Also preferably, the slits 5e have a maximum width of about 0.05 to 0.5 mm at the distal end (as measured in a circumferential direction) and a length of about 50 to 200 mm (as measured in a longitudinal direction).

Also the distal portion of the metal tube is not limited to the shape shown in FIG. 14 while either a distal zone with parallel slits of fixed width as shown in FIG. 7 or a beveled distal zone as shown in FIG. 8 may be employed.

The vascular dilatation instrument 41 of this embodiment includes an outer tube 2 having an identical outer diameter throughout its length. If desired, the outer tube 2 may be provided with a distal portion having a smaller diameter than the remainder as in the embodiment of FIG. 1. The outer tube 2 may be either a synthetic resin tube or a composite body of synthetic resin tube and superelastic metal tube.

Figure 16:
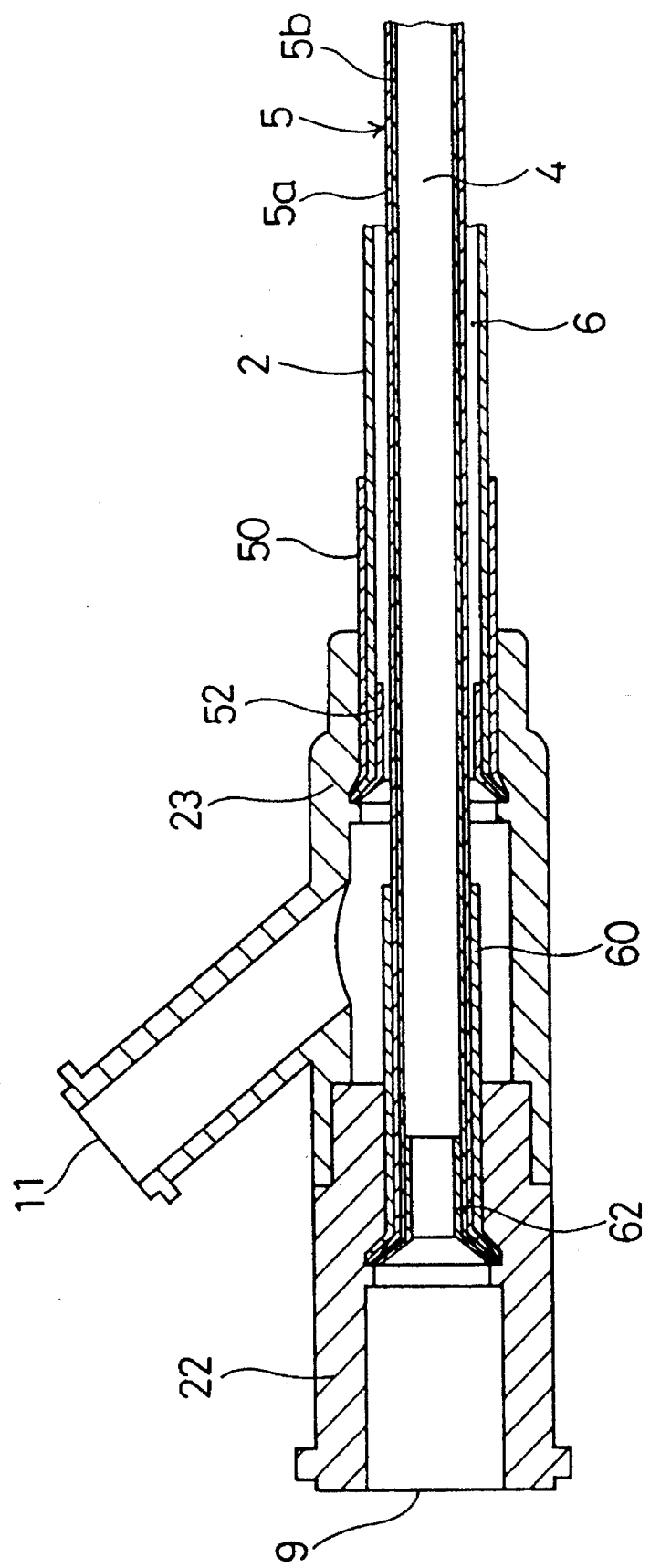
FIG. 16 is an enlarged cross-sectional view of the proximal portion of the instrument shown in FIG. 13.

As shown in FIGS. 13 and 16, a branch hub or adapter 20 is attached to the proximal end of the instrument. The branch hub 20 includes fixedly mated inner and outer hub segments 22 and 23. The inner hub segment 22 is fixedly connected to the inner tube 5 (which is a composite body of synthetic resin tube 5a and superelastic metal tube 5b) and has a first opening 9 in communication with the first lumen 4 and forming a guide wire port. The outer hub segment 23 is fixedly connected to the outer tube 2 and has a second opening 11 in communication with the second lumen 6 and forming an injection port.

Although part of the resin material of which the resin tube 5a is made may flow into the slits 5e in the superelastic metal tube 5b, it is preferred that the slits 5e be substantially free of the resin material and void. In the absence of the resin material flowing into the slits, deformation of the metal tube 5b is never obstructed.

The remaining components are substantially the same as in the instrument 1 of the first embodiment.

Figure 17:
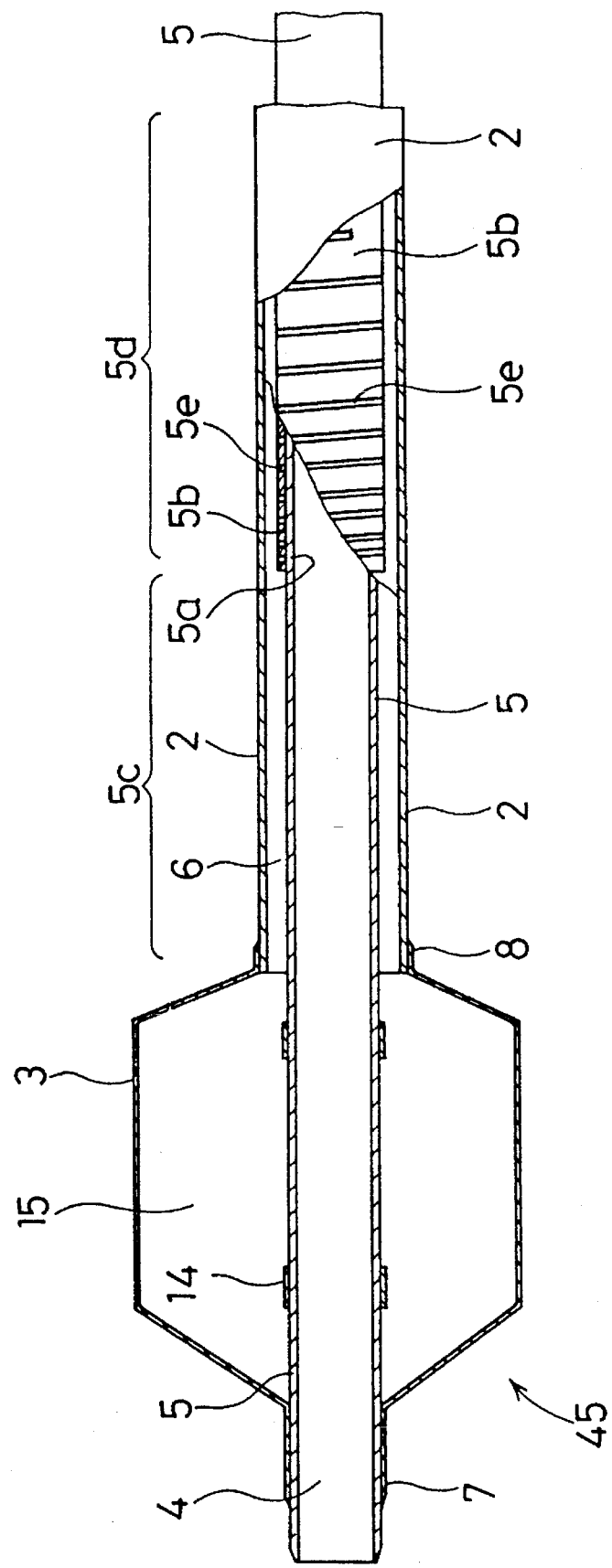
FIG. 17 is an enlarged cross-sectional view of a modified distal portion of a vascular dilatation instrument according to the invention.

FIG. 17 illustrates a vascular dilatation instrument according to a further embodiment of the invention. The basic construction of this embodiment is the same as that shown in FIGS. 13 to 16 and like parts are designated by the same numerals as in FIGS. 13 to 16. The difference is the shape of slits in the superelastic metal tube of the inner tube. More particularly, the vascular dilatation instrument 45 of this embodiment includes an inner tube 5 which includes a synthetic resin tube 5a and a superelastic metal tube 5b having a distal zone where a spiral slit 5e is formed. The provision of spiral slit 5e makes the distal zone of the metal tube 5b more flexible and bendable. The flexible distal zone of the metal tube 5b is effective for reducing the difference in physical properties between the superelastic metal tube 5b and the synthetic resin tube 5a, thereby preventing separation and differential motion therebetween. The instrument is more smooth and easy to manipulate.

The slit width is not fixed since it is determined in consideration of the outer diameter of the outer tube or the like. The slit width is preferably about 0.1 to 1.5 mm, more preferably 0.5 to 1.0 mm. The slit width is preferably about ⅙ to ⅔, more preferably ⅓ to ½ of the outer diameter of the metal tube. Within this range, the metal tube distal zone is fully flexible and not broken during operation. Where the spiral slit 5e has a constant pitch, the pitch is preferably about 0.2 to 2.0 mm, more preferably 0.3 to 0.5 mm because within this range, the metal tube distal zone is fully flexible and not broken during operation. The extent of the distal portion of the metal tube where the slit is formed is determined by taking into account the instrument length or the like. Typically the slit is formed in a distal region of the metal tube which extends about 100–1,000 mm, preferably 150–500 mm from the distal edge thereof.

In a preferred example, the spiral slit 5e is formed at increasing pitches. As shown in FIG. 17, the slit pitch is shorter at the distal end (left-hand side) and longer at the proximal end (right-hand side) of the distal zone. Then the superelastic metal tube 5b becomes more flexible toward the distal end. Such a gradual change of physical properties ensures smoother bending of the metal tube distal zone and easier manipulation of the instrument. Where the slit has a varying pitch, the pitch is preferably about 0.3 to 2.0 mm at the distal end and about 5 to 10 mm at the proximal end of the slit zone, and an intermediate value at an intermediate region. It is also acceptable that the pitch be continuously increased from the distal end toward the proximal end. Within this range, the metal tube distal zone is fully flexible and not broken during operation. A single spiral slit is formed in the embodiment of FIG. 17 although two or more slits may be formed.

The slit 5e may have another shape, for example, a spiral slit whose width is greater at the distal end than at the proximal end as found in the instrument 37 shown in FIG. 10. Instead of the slit, perforations may be provided as in the embodiment of FIG. 11.

Figure 18:
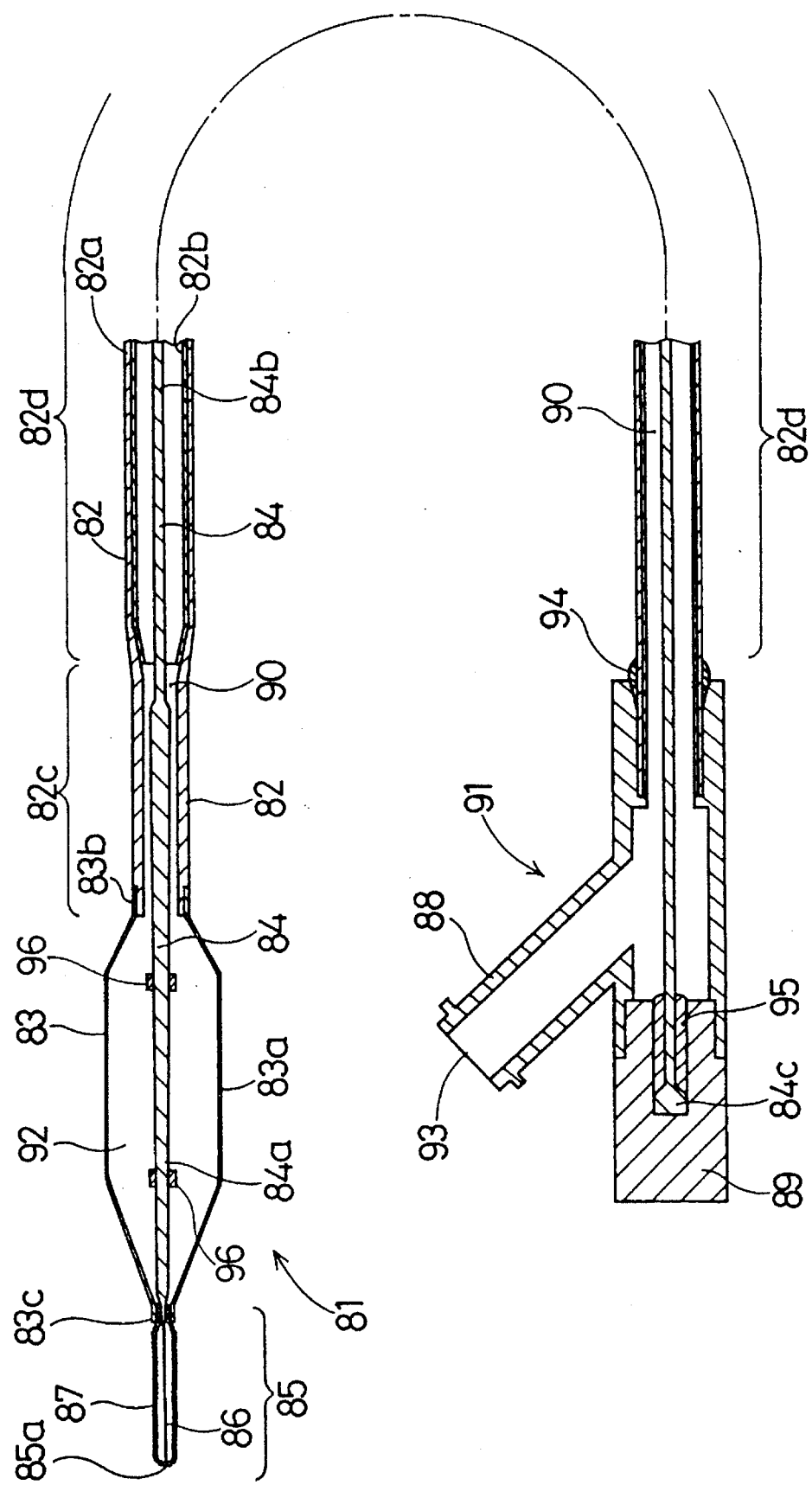
FIG. 18 is an overall, partially omitted, cross-sectional view of a vascular dilatation instrument according to a further embodiment of the invention.

FIG. 18 illustrates in a schematic cross-sectional view a vascular dilatation instrument according to the second aspect of the invention.

The vascular dilatation instrument generally designated at 81 is illustrated as comprising a tubular member 82 defining a lumen 90 therethrough and having an opening in fluid communication with the lumen 90, a leading head 87, and an inflatable member 83 having one end 83b attached to the tubular member 82 and another end 83a attached to the leading head 87 and defining an interior space in fluid communication with the lumen 90 through the opening. The tubular member 82 includes a main body section 82d based on a superelastic metal tube 82b and a distal section 82c made of a synthetic resin. The superelastic metal tube 82b includes a deformable distal zone which is more flexible than the remainder.

Figure 19:
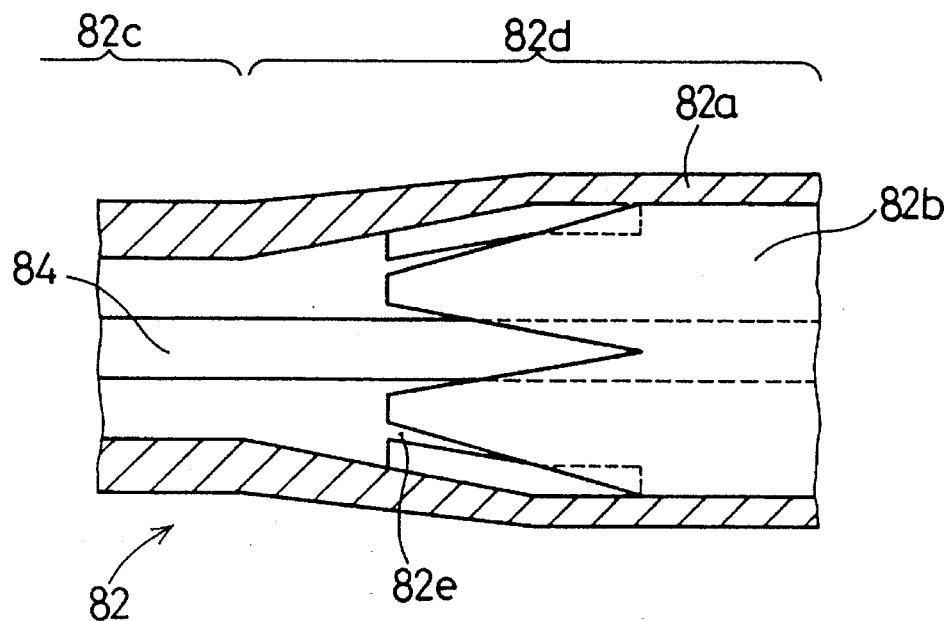
FIG. 19 is an enlarged cross-sectional view of a portion of the instrument shown in FIG. 18.

In the enlarged view of FIG. 19 is shown the transition between the main and distal sections 82d and 82c of the tubular member 82.

The vascular dilatation instrument 81 includes a main body including a tubular member 82, a dilator 83, an elastic core 84, and a leading head 87 and a hub or adapter 91.

In the instrument 81, the tubular member 82 includes a main body section 82d consisting of a superelastic metal tube 82b and a synthetic resin tube and a distal section 82c consisting of the synthetic resin tube. The transition between the main body section 82d and the distal section 82c which corresponds to a distal zone of the superelastic metal tube 82b is a deformable zone which is more flexible than the remainder of the metal tube.

More particularly, the tubular member 82 includes the superelastic metal tube 82b and the synthetic resin tube 82a surrounding and covering the outside surface of the metal tube 82b in the main body section. The synthetic resin tube 82a protrudes beyond the distal end of the superelastic metal tube 82b to form the distal section 82c of the tubular member 82.

As shown in FIG. 18 and FIG. 19 which is an enlarged cross-sectional view of the transition between the main and distal sections 82d and 82c, the superelastic metal tube 82b in a distal zone is provided with a plurality of slits 82e extending from the distal end toward the proximal end. The provision of slits 82e makes the distal zone of the metal tube more flexible than the remainder. As shown in FIG. 19, the slits 82e are gradually decreased in width from the distal end to the proximal end of the distal zone of the superelastic metal tube 82b, or differently stated, gradually increased in width toward the distal end. The slit has the maximum width at the distal end of the metal tube 82b. Then as one goes toward the distal end, the superelastic metal tube 82b is more flexible and deformable and the side wall is more deformable radially inward and outward. Preferably two to eight slits 82e are formed at approximately equal intervals. Also preferably, the slits 82e have a maximum width of about 0.05 to 0.5 mm at the distal end and a length of about 50 to 200 mm.

In the vascular dilatation instrument 81 of the illustrated embodiment, the superelastic metal tube 82b includes the distal zone which is tapered as shown in FIGS. 18 and 19. More particularly, the side wall defining the distal zone where the slits are formed is bent radially inward. This tapered distal zone can be formed by working the slit distal zone of the metal tube 82b to the configuration shown in FIG. 19. Alternatively, the synthetic resin tube 82a is molded or fitted over the metal tube 82b such that the outer diameter of that portion of the resin tube 82a surrounding the metal tube distal zone is reduced. That is, the metal tube distal zone is deformed radially inward by the resin tube 82a. Then that portion of the resin tube 82a extending forward (leftward in FIGS. 18 and 19) beyond the metal tube 82b has a smaller diameter than that portion of the resin tube 82a around the metal tube 82b. Since the distal or protruding portion 82c formed solely of the resin tube 2a has a smaller diameter than the main body portion including the metal tube 82b, it becomes possible to insert the distal portion of the vascular dilatation instrument 81 into a vessel on a more peripheral side. Since the transition between the main body section 82d and the distal section 82c of the tubular member 82 (which corresponds to the distal end of the main body section 82d) is tapered forward, insertion into a vessel is facilitated.

Since the main body section 82d of the tubular member 82 has the superelastic metal tube, the vascular dilatation instrument 81 is effective for transmitting the translational and torsional forces from the proximal end to the distal end of the instrument, that is, improved in pushability and torque transmission. The distal section 82c made of synthetic resin has sufficient flexibility. The transition between the main body section 82d and the distal section 82c of the tubular member 82 (which corresponds to the distal end of the superelastic metal tube 82b) is a more flexible, deformable zone and is effective in preventing angular bending at the interface between the rigid main body section and the flexible distal section.

The tubular member 82 is disposed coaxial with and around the elastic core or shaft 84 and includes the distal section 82c which terminates at a position retracted a predetermined distance from the distal end of the shaft 84.

The tubular member 82 includes the main body section 82d consisting of the superelastic metal tube 82b and the synthetic resin tube 82a surrounding and covering the outside surface of the metal tube 82b and the distal section 82c consisting solely of the synthetic resin tube 82a. Differently stated, the tubular member 82 includes the superelastic metal tube 82b and the synthetic resin tube 82a surrounding and covering the outside surface of the metal tube 82b while the synthetic resin tube 82b protrudes beyond the distal end of the superelastic metal tube 82b to form the distal section 82c of the tubular member 82.

Typically the tubular member 82 has a length of about 300 to 4,000 mm, preferably 500 to 1,600 mm and an outer diameter of about 0.3 to 1.5 mm, preferably 0.4 to 1.2 mm.

The superelastic or pseudoelastic metal tube 82b is preferably made of a superelastic alloy. The superelastic alloys are generally known as shape memory alloys and exert superelasticity at the living body temperature (about 37° C.) or higher. Preferred examples of the superelastic alloy include Ti—Ni binary alloys consisting essentially of 49 to 53 atom % of nickel and the balance of titanium, Cu—Zn binary alloys consisting essentially of 38.5 to 41.5% by weight of zinc and the balance of copper, Cu—Zn—X ternary alloys containing 1 to 10% by weight of X wherein X is Be, Si, Sn, Al or Ga, and Ni—Al binary alloys consisting essentially of 36 to 38 atom % of aluminum and the balance of nickel, with the Ti—Ni alloys being most preferred. Mechanical properties may be properly controlled by replacing part of Ti—Ni alloy by 0.01 to 10.0 atom % of X to form Ti—Ni—X alloys wherein X is Co, Fe, Mn, Cr, V, Al, Nb, W or B or replacing part of Ti—Ni alloy by 0.01 to 30.0 atom % of X to form Ti—Ni—X alloys wherein X is Cu, Pd or Zr and/or selecting the conditions of cold working and/or final heat treatment. By the term "superelasticity" it is meant that when an alloy is deformed (bent, stretched or compressed) at service temperature to the extent where conventional metals undergo plastic deformation and then released from deformation, the alloy resumes the original shape without a need for heating.

Typically the superelastic metal tube 82b has an outer diameter of about 0.2 to 1.5 mm, preferably 0.3 to 1.2 mm, a wall thickness of about 30 to 200 μm, preferably 50 to 150 μm, a length of about 350 to 4,000 mm, preferably 550 to 1,800 mm, a buckling strength (yield stress under load) of about 5 to 200 kg/mm$^2$, preferably 8 to 150 kg/mm$^2$ at 22° C., and a restoring stress (yield stress upon unloading) of about 3 to 180 kg/mm$^2$, preferably 5 to 130 kg/mm$^2$ at 22° C.

For the synthetic resin tube 82a, materials having flexibility are used, for example, thermoplastic resins such as polyolefins (e.g., polyethylene, polypropylene, ethylene-propylene copolymers, and ethylene-vinyl acetate copolymers), polyvinyl chloride, polyamide elastomers, and polyurethane, and polyimides. Preferred are the polyolefins and polyimides. That portion of the synthetic resin tube 82a surrounding and covering the superelastic metal tube 82b preferably has a wall thickness of about 5 to 300 μm, more preferably 10 to 200 μm.

Alternatively, a heat-shrinkable tube may be used as the synthetic resin tube 82a of the tubular member 82. The heat-shrinkable tube used herein is a tube which has an inner diameter larger than the outer diameter of the superelastic metal tube 82b prior to heating and thus allows the superelastic metal tube to be inserted therethrough, but on heating, shrinks substantially uniformly over its entirety to come in close contact with the outside surface of the metal tube. Such a heat-shrinkable tube is preferably prepared by molding a resin into a tube having an inner diameter equal to or slightly smaller than the outer diameter of the superelastic metal tube, and expanding the tube over its entirety so as to increase its diameter so that upon heating, it may shrink to a diameter equal to or substantially equal to the diameter as molded. The heat-shrinkable tube is made of the material which can be expanded, but shrinks upon heating as mentioned above, for example, polyolefins (e.g., polyethylene, polypropylene, and ethylene-propylene copolymers), ethylene-vinyl acetate copolymers, and polyamide elastomers.

Although part of the resin material of which the resin tube 82a is made may flow into the slits 82e in the superelastic metal tube 82b, it is preferred that the slits 82e be substantially free of the resin material and empty. In the absence of the resin material flowing into the slits, flexural motion of the metal tube 82b is never obstructed.

Preferably, markers 96 are provided on the outside surface of the elastic shaft 84 for radiological localization purposes. More particularly, the markers 96 are disposed in alignment with the opposed ends of the cylindrical portion of the inflatable member 83 as shown in FIG. 18. The markers 14 are in the form of coil springs or rings made of a radiographic high contrast material, for example, platinum, platinum alloys, tungsten, tungsten alloys, silver and silver alloys.

The elastic core or shaft 84 is an elongated member having a distal end and a proximal end and extending throughout the tubular member 82, with the leading head 85 secured to the distal end. In the embodiment illustrated in FIG. 18, the elastic shaft 84 includes a main body section of the shaft 84 corresponding to the main body section 82d of the tubular member 82 and a distal section 84a which includes a base portion 84b corresponding to the distal section 82c of the tubular member 82 and a tip portion corresponding to the inflatable member 83.

More particularly, the leading head 85 which is attached to the distal end of the elastic shaft 84 includes a wire 86 axially extending from the distal end of the shaft 84 and a coil spring 87 enclosing the wire 86 and secured to the wire 86 at opposed ends. The wire 86 prevents stretching of the coil spring 87. Desirably the distal section 84a of the elastic shaft 84 is more flexible toward the distal extremity (the left end in FIG. 18). To this end, the shaft 84 is reduced in diameter toward the distal extremity. The shaft 84 has a relatively small diameter in the main body section and a relatively large diameter in the base portion 84b, with the diameter gradually decreasing from the base portion 84b to the tip portion. The base portion 84b of the elastic shaft distal section has a larger diameter than the main body section of the shaft 84 for the purpose of preventing angular folding of the distal section 82c of the tubular member 82 (consisting solely of synthetic resin tube). As a result, the space or lumen 90 between the tubular member 82 and the shaft 84 is narrow around the base portion 84b.

Useful for the elastic core or shaft 84 are stainless steel (preferably highly tensile stainless steel for springs), tungsten, tungsten-cobalt alloys, piano wire (preferably nickel or chromium plated piano wire), and superelastic alloys. Preferred examples of the superelastic alloy include Ti—Ni binary alloys consisting essentially of 49 to 53 atom % of nickel and the balance of titanium, Cu—Zn binary alloys consisting essentially of 38.5 to 41.5% by weight of zinc and the balance of copper, Cu—Zn—X ternary alloys containing 1 to 10% by weight of X wherein X is Be, Si, Sn, Al or Ga, and Ni—Al binary alloys consisting essentially of 36 to 38 atom % of aluminum and the balance of nickel, with the Ti—Ni alloys being most preferred. Mechanical properties may be properly controlled by replacing part of Ti—Ni alloy by 0.01 to 10.0 atom % of X to form Ti—Ni—X alloys wherein X is Co, Fe, Mn, Cr, V, Al, Nb, W or B or replacing part of Ti—Ni alloy by 0.01 to 30.0 atom % of X to form Ti—Ni—X alloys wherein X is Cu, Pd or Zr and/or selecting the conditions of cold working and/or final heat treatment. By the term "superelasticity" it is meant that when an alloy is deformed (bent, stretched or compressed) at service temperature to the extent where conventional metals undergo plastic deformation and then released of stresses, the alloy resumes the original shape without a need for heating.

Typically the elastic shaft 84 has a length of about 350 to 4,000 mm, preferably 550 to 1,800 mm, a buckling strength (yield stress under load) of about 30 to 100 kg/mm$^2$, preferably 40 to 55 kg/mm$^2$ at 22° C., and a restoring stress (yield stress upon unloading) of about 20 to 80 kg/mm$^2$, preferably 30 to 55 kg/mm$^2$ at 22° C. The distal section 84a of the shaft 84 has an outer diameter of about 0.1 to 1.0 mm, preferably 0.15 to 0.7 mm, a bending load of about 0.1 to 10 g, preferably 0.3 to 6.0 g, and a restoring load of about 0.1 to 10 g, preferably 0.3 to 6.0 g.

These values are not critical. The distal section 84a of the shaft 84, which is moderately pointed, need not have an outer diameter within the above-mentioned range and may locally have such an outer diameter. The main and distal section of the shaft need not have an identical value of restoring stress and it is rather preferred that the shaft is locally heat treated such that different regions may have appropriate physical properties for their diameter. Preferably the main and distal sections of the shaft are separately heat treated such that the main section may have a greater restoring stress and the distal section be flexible. The elastic shaft need not be a single wire member. Shafts consisting of parallel extending or braided wires are also useful. Such a multi-wire shaft may also be modified to have the above-mentioned functions, that is, such that physical properties are changed stepwise or continuously.

The leading head 85 is to lead or guide the vascular dilatation instrument 81 to the destined vascular site. It is formed by the coil spring 87 in the embodiment illustrated in FIG. 18. The leading head 85 should be flexible such that when the leading edge (the left end in FIG. 18) of the head 85 abuts against a blood vessel wall, the head readily flexes to find a way forward in another direction without concentrating stresses at the leading edge. Since the leading head 85 is also the distal end of the vascular dilatation instrument 81, it is preferred that the head be readily located under radiological observation. In this regard, the head 85 is preferably made of a radiographic high contrast material, for example, platinum, platinum alloys, tungsten, tungsten alloys, silver and silver alloys.

As mentioned above, the leading head 85 should preferably be flexible. In this regard, the coil spring 87 may be made of superelastic or pseudoelastic metal wires or elastic metal wires. Preferably the head 85 has an outer diameter of about 0.2 to 1.0 mm and a length of about 2 to 50 mm. When the head is made of a superelastic metal wire, it preferably has a buckling strength (yield stress under load) of about 5 to 200 kg/mm$^2$, preferably 8 to 150 kg/mm$^2$ at 22° C. and a restoring stress (yield stress upon unloading) of about 3 to 180 kg/mm$^2$, preferably 5 to 150 kg/mm$^2$ at 22° C.

The leading edge 85a of the leading head 85 is preferably formed as a head piece having a blunt convex curved surface by heating and melting the coiled fine metal wire. The coil spring 87 forming the head 85 is joined to the distal end of the shaft 84 by brazing. Instead of the wire 86 for preventing the coil spring 87 from stretching, the shaft 84 may be extended to reach the leading edge of the head 85 where the end of the extension is secured to the coil spring 87.

The inflatable member or dilator 83 has one end 83c attached to the proximal end of the leading head 87 and another end 83b attached to the distal end of the tubular member 82. The inflatable member 83 defines an interior space 92 which is in flow communication with the lumen 90 defined between the tubular member 82 and the elastic shaft 84 through the distal opening of the tubular member 82 so that a fluid can be fed into the interior space of the member 83 for inflation. The inflatable member 83 is a contractible or foldable sleeve membrane and includes a substantially cylindrical portion 83a having an approximately uniform diameter at least a part of which is substantially cylindrical, when inflated, for dilating the stricture in a blood vessel and is foldable in close contact with the shaft 84 when deflated. The cylindrical portion 83a need not be completely cylindrical, but may be polygonal.

With respect to the dimensions of the inflatable member 83, the cylindrical portion 83a when inflated preferably has an outer diameter of about 1.0 to 10.0 mm, more preferably 1.0 to 5.0 mm and a length of about 5 to 50 mm, more preferably 10 to 40 mm. The inflatable member 83 preferably has an overall length of about 10 to 70 mm, more preferably 15 to 60 mm.

For the inflatable member 83, materials having a certain degree of flexibility and capable of dilating the stricture are used, for example, thermoplastic resins such as polyolefins (e.g., polyethylene, polypropylene, and ethylene-propylene copolymers), polyesters (e.g., polyethylene terephthalate), polyvinyl chloride, ethylene-vinyl acetate copolymers, crosslinked ethylene-vinyl acetate copolymers, polyurethane, and polyamide elastomers, and silicone rubber and latex rubber.

As shown in FIG. 18, the branch hub 91 is attached to the proximal end of the instrument. The branch hub 91 includes fixedly mated first and second hub segments 88 and 89. The first segment 88 is fixedly connected to the tubular member 82 at the proximal end with an adhesive 94 and has a first opening 93 in communication with the lumen 90 and forming a port for injecting a fluid for inflation. The second segment 89 is fixedly connected to the elastic shaft 84 at the proximal end. More particularly, the second segment 89 defines a cylindrical cavity which receives a diametrically enlarged portion 84c of the shaft 84 at its proximal end. The proximal end of the shaft 84 including the enlarged portion 84c is secured within the second segment cavity with an adhesive 95.

The first and second hub segments 88 and 89 are engaged as shown in FIG. 18. This engagement is achieved by attaching the first segment 88 to the proximal end of the tubular member 82, attaching the second segment 89 to the proximal end of the shaft 84, inserting the shaft 84 from its distal end into the lumen 90 of the tubular member 82 at the rear end until the second segment 89 contacts the first segment 88, and tightly coupling the first and second segments 88 and 89. At this point, an adhesive may be applied to the interface between the first and second segments 88 and 89 to form a firm joint.

The branch hub 91 is made of thermoplastic resins such as polyolefins (e.g., polyethylene and polypropylene), polycarbonates, polyamides, polysulfones, polyarylates, butylene-styrene copolymers, and methacrylate-butylene-styrene copolymers.

Preferably the tubular member 82, inflatable member 83 and leading head 85 on their outside surface are treated so that the outside surface may exhibit lubricity. Such treatments include coating and fixation of hydrophilic polymers such as poly(2-hydroxyethyl methacrylate), poly(hydroxyethyl acrylate), hydroxypropyl cellulose, methyl vinyl ether-maleic anhydride copolymers, polyethylene glycol, polyacrylamide, and polyvinyl pyrrolidone.

Figure 20:
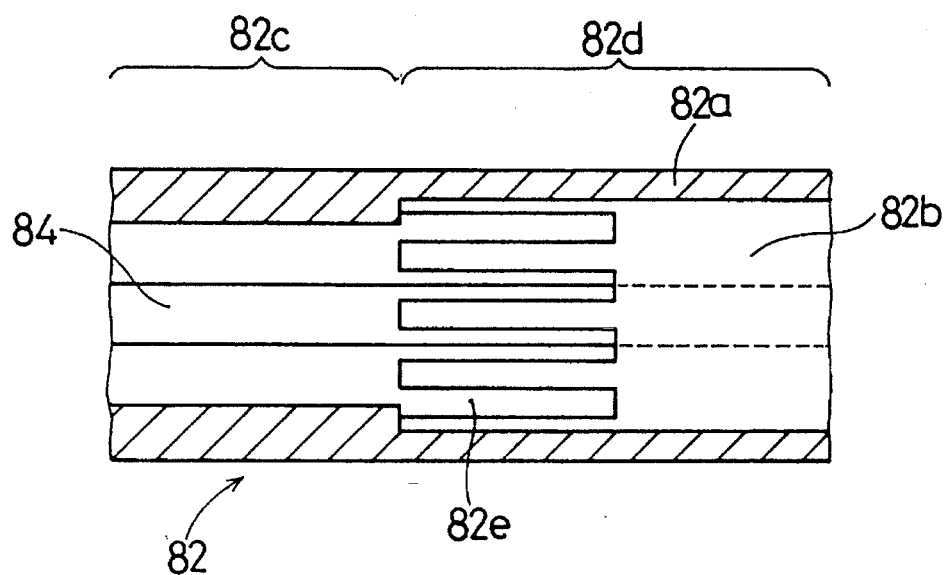
FIGS. 20, 21, 22, and 23 are enlarged cross-sectional views similar to FIG. 19, showing different examples.

The structure of the tubular member 82 is not limited to that shown in FIGS. 18 and 19. Another exemplary structure of the tubular member is shown in FIG. 20. Unlike the embodiment of FIG. 19, a vascular dilatation instrument of this embodiment includes a tubular member 82 having a substantially identical outer diameter over its entirety. The tubular member 82 includes a superelastic metal tube 82b having slits 82e formed at a distal zone thereof as in FIG. 19, but having an identical width while extending parallel from the distal end to the proximal end of the flexible zone. Preferably two to eight slits 82e are formed at substantially equal intervals. The slits 82e preferably have a circumferential width of about 0.05 to 0.5 mm and a length of about 50 to 200 mm.

Also the distal portion of the metal tube 82b can be a beveled distal portion as shown in FIG. 8 wherein the metal tube is cut at an angle of about 5° to 45° with respect to its axis.

Figure 21:
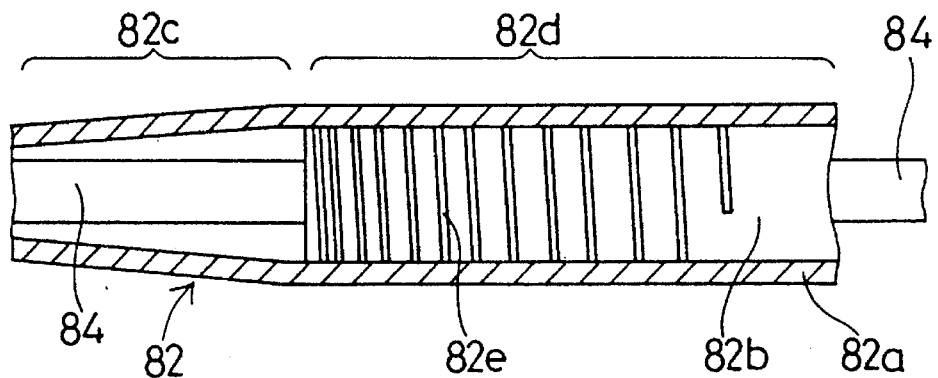

Another exemplary structure of the tubular member 82 is shown in FIG. 21.

In the vascular dilatation instrument of the embodiment shown in FIG. 21, the tubular member 82 includes a synthetic resin tube 82a and a superelastic metal tube 82b having a distal zone where a spiral slit 82e is formed. The provision of spiral slit 82e makes the distal zone of the metal tube 82b more flexible and bendable. The flexible distal zone of the metal tube 82b is effective for reducing the difference in physical properties between the superelastic metal tube 82b and the synthetic resin tube 82a, thereby preventing separation and differential motion therebetween. The instrument is more smooth and easy to manipulate.

The slit width is not fixed since it is determined in consideration of the outer diameter of the tubular member or the like. The slit width is preferably about 0.1 to 1.5 mm, more preferably 0.5 to 1.0 mm. In other words, the slit width is preferably about ⅙ to ⅔, more preferably ⅓ to ½ of the outer diameter of the metal tube. Within this range, the metal tube distal zone is fully flexible and not broken during operation. Where the spiral slit 82e has a constant pitch, the pitch is preferably about 0.2 to 2.0 mm, more preferably 0.3 to 0.5 mm because within this range, the metal tube distal zone is fully flexible and not broken during operation. The extent of the distal portion of the metal tube where the slit is formed is determined by taking into account the length of the instrument or the like. Typically the slit is formed in a distal region of the metal tube which extends 100–1,000 mm, preferably 150–500 mm from the distal edge thereof.

In a preferred example, the spiral slit 82e is formed at increasing pitches. As shown in FIG. 21, the slit pitch is shorter at the distal end (left-hand side) and longer at the proximal end (right-hand side). Then the distal zone of the superelastic metal tube 82b becomes more flexible toward the distal end. Such a gradual change of physical properties ensures smoother bending of the metal tube distal zone and easier manipulation of the instrument. Where the slit has a varying pitch, the pitch is preferably about 0.3 to 2.0 mm at the distal end and about 5 to 10 mm at the proximal end of the slit region, and an intermediate value at an intermediate region. It is also acceptable that the pitch be continuously increased from the distal end toward the proximal end. Within this range, the metal tube distal zone is fully flexible and not broken during operation.

A single spiral slit is formed in the embodiment of FIG. 21 although two or more slits may be formed. Also employable is a spiral slit having an increased width at the distal end and a reduced width at the proximal end as shown in FIG. 10.

Figure 22:
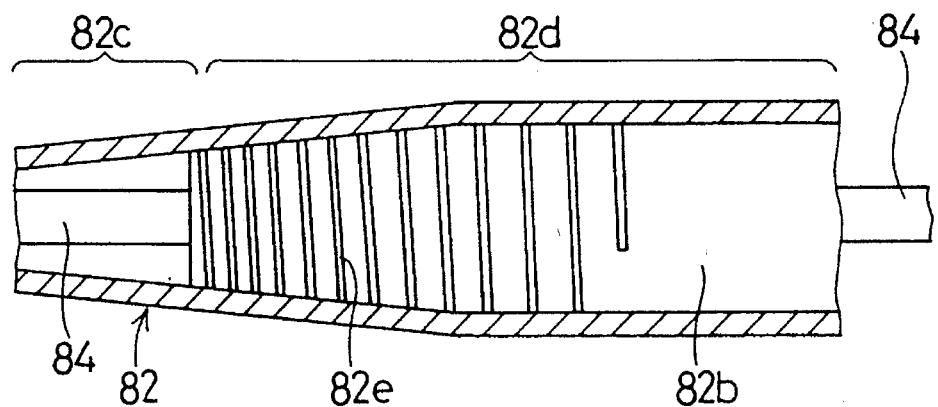

FIG. 22 shows a further exemplary structure of the tubular member 82. The superelastic metal tube 82b of the tubular member 82 includes a distal zone which is tapered or diametrically reduced toward the distal end (left-hand end in FIG. 22). A spiral slit 82e is formed in the tapered distal zone of the metal tube 82b. This spiral slit 82e has a reduced pitch at the distal end and an increased pitch at the proximal end of the distal zone.

Figure 23:
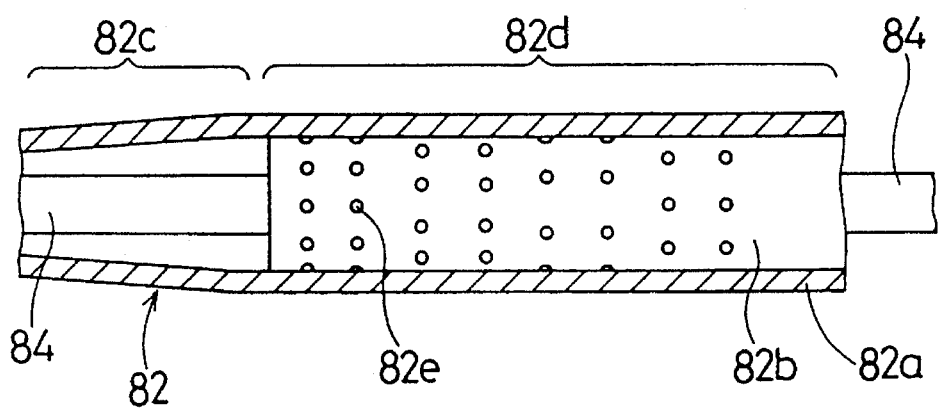

FIG. 23 shows a still further exemplary structure of the tubular member 82. The superelastic metal tube 82b of the tubular member 82 includes a distal zone which is perforated with a plurality of holes 82e. Preferably more holes 82e are distributed at the distal end than at the proximal end of the distal zone of the metal tube 82b as shown in FIG. 23.

The diameter of perforations 82e is not fixed since it is determined in accordance with the number of perforations, the outer diameter of metal tube and the like. Typically the perforations 82e have a diameter of about 0.1 to 0.4 mm, preferably 0.2 to 0.3 mm. The pore diameter is preferably about ⅒ to ⅓ of the outer diameter of the metal tube. Within this range, the metal tube distal zone is fully flexible and not broken during operation. The perforations 82e are preferably spaced a distance of about 0.1 to 0.5 mm. Within this range, the metal tube distal zone is fully flexible and not broken during operation. Where the perforation distribution is varied over the distal zone, the spacing between perforations preferably is about 0.1 to 0.2 mm at the distal end and about 0.3 to 0.5 mm at the proximal end. In an intermediate region between the distal and proximal ends, the spacing between perforations has an intermediate value or is gradually varied. The extent of the distal portion of the metal tube where the perforations are formed is determined by taking into account the length of the instrument or the like. Typically the perforations are formed in a distal region of the metal tube which extends about 100–1,000 mm, preferably 150–500 mm from the distal edge thereof.

Instead of the varying perforation distribution, the diameter or area of perforations may be varied such that the diameter or area is greater near the distal end than near the proximal end of the metal tube distal zone.

With respect to the shape, the perforations need not be true circle and may be ellipsoidal, for example, oval holes elongated in a circumferential or axial direction of the metal tube or polygonal such as square or pentagonal holes. Each perforation preferably has an area of 0.007 to 0.13 mm².

Although part of the resin material of which the resin tube 82f is made may flow into the perforations 82e in the superelastic metal tube 82b, it is preferred that the perforations 82e be substantially free of the resin material and empty. In the absence of the resin material flowing into the perforations, flexural motion of the metal tube 82b is never obstructed.

Next, a catheter according to the third aspect of the invention is described.

Figure 24:
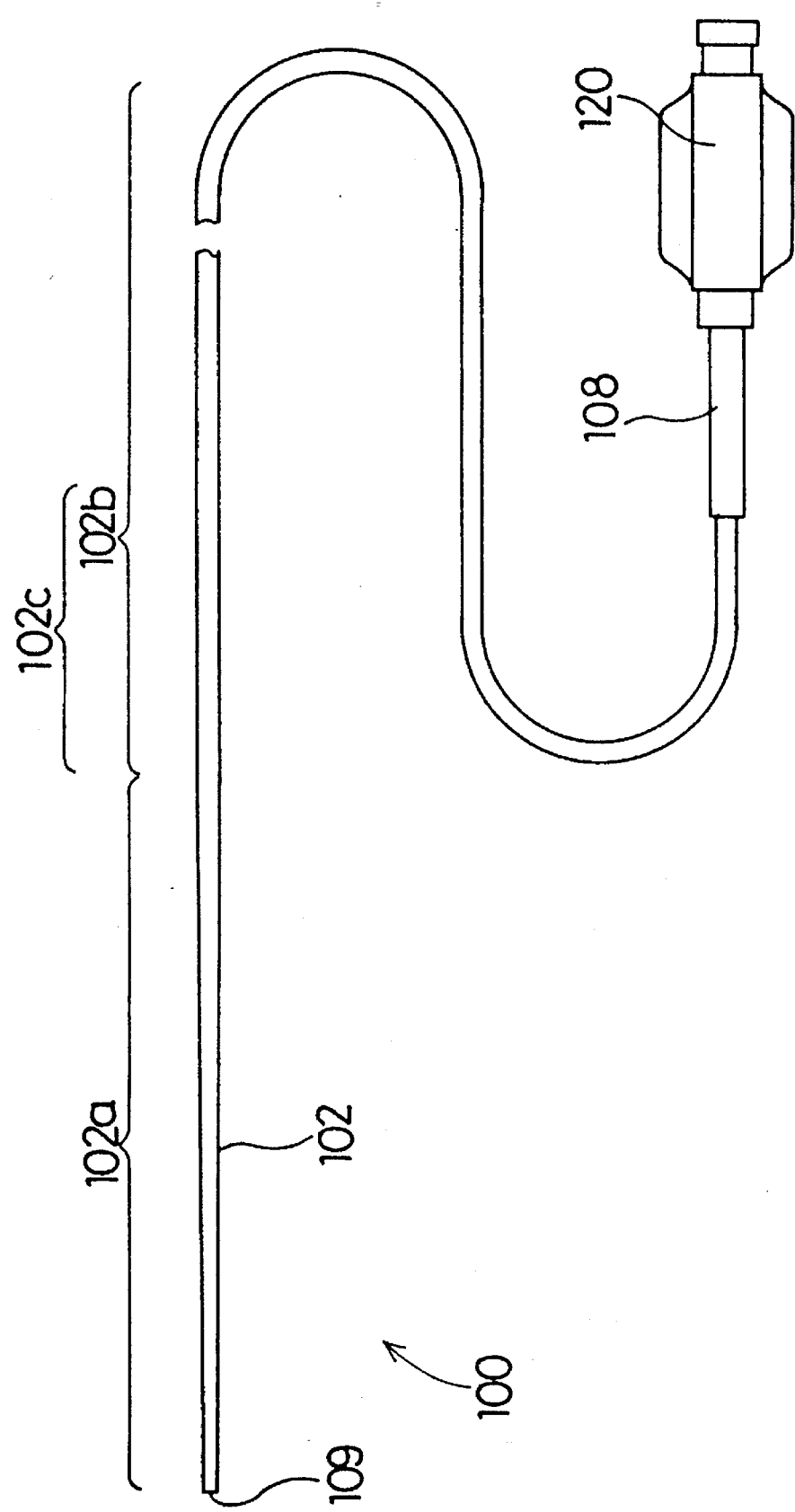
FIG. 24 is an overall, partially omitted, schematic view of a catheter according to a still further embodiment of the invention.
Figure 25:
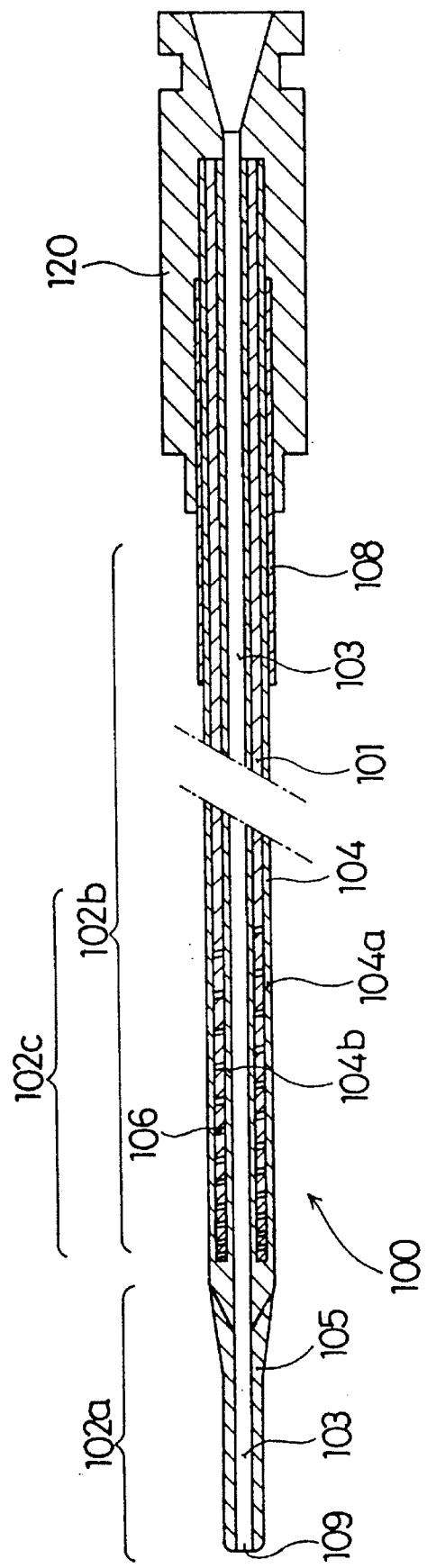
FIG. 25 is a cross-sectional view of distal and proximal portions of the catheter shown in FIG. 24.

Referring to FIGS. 24 and 25, there is illustrated a catheter generally designated at 100 as comprising a main body section 102b including a superelastic metal tube 101 and a synthetic resin layer 104 covering the metal tube 101, and a distal section 102a made of a synthetic resin. The superelastic metal tube 101 includes a distal zone 102c which is provided with a slit 106 or a plurality of perforations 107 (see FIG. 32). The distal zone 102c is more flexible and deformable than the remainder.

Since the main body section 102b has the superelastic metal tube 101 therein, the catheter is effective for transmitting translational and torsional forces from the proximal end to the distal end, that is, improved in pushability and torque transmission. Then the catheter over its entirety can be reduced in wall thickness and hence in diameter. The distal zone 102c of the superelastic metal tube 101 is provided with a slit 106 or a plurality of perforations 107 and thus forms a flexible zone which mitigates the change in physical properties between the superelastic metal tube 101 and the distal section solely of synthetic resin tube, thereby preventing angular folding at the interface therebetween. The catheter is more smooth and convenient to insert or manipulate and will not cause damage to a vascular wall upon insertion. The provision of a spiral slit or perforations makes the distal zone of the metal tube more flexible and bendable. The flexible distal zone of the metal tube 101 is effective for reducing the difference in physical properties between the superelastic metal tube 101 and the synthetic resin layer 104, thereby preventing separation and differential motion therebetween. The catheter is more smooth and convenient to manipulate.

The catheter of the invention finds use as vascular insertion catheters, typically vasographic catheters for heart and brain blood vessels and medication catheters for administering medicament to heart and brain blood vessels.

In the embodiment of FIGS. 24 and 25, the catheter 100 is illustrated as a medication catheter for administering medicament to heart and brain blood vessels.

The catheter 100 having distal and proximal ends includes the main body section 102b and the distal section 102a. It also includes a lumen 103 extending from the proximal end to the distal end where a distal opening 109 is defined.

The main body section 102b includes the superelastic metal tube 101 and synthetic resin layers 104a and 104b covering the outside and inside surfaces of the metal tube 101. The distal section 102a is a tip member 105 made of synthetic resin which is fixedly connected to the distal end of the main body section 102b.

The superelastic metal tube 101 is preferably made of a superelastic alloy. The superelastic alloys are generally known as shape memory alloys and exert superelasticity at the living body temperature (about 37° C.) or higher. Preferred examples of the superelastic alloy include Ti—Ni binary alloys consisting essentially of 49 to 53 atom % of nickel and the balance of titanium, Cu—Zn binary alloys consisting essentially of 38.5 to 41.5% by weight of zinc and the balance of copper, Cu—Zn—X ternary alloys containing 1 to 10% by weight of X wherein X is Be, Si, Sn, Al or Ga, and Ni—Al binary alloys consisting essentially of 36 to 38 atom % of aluminum and the balance of nickel, with the Ti—Ni alloys being most preferred. Mechanical properties may be properly controlled by replacing part of Ti—Ni alloy by 0.01 to 10.0 atom % of X to form Ti—Ni—X alloys wherein X is Co, Fe, Mn, Cr, V, Al, Nb, W or B or replacing part of Ti—Ni alloy by 0.01 to 30.0 atom % of X to form Ti—Ni—X alloys wherein X is Cu, Pd or Zr and/or selecting the conditions of cold working and/or final heat treatment. By the term "superelasticity" it is meant that when an alloy is deformed (bent, stretched or compressed) at service temperature to the extent where conventional metals undergo plastic deformation and then released from deformation, the alloy resumes the original shape without a need for heating.

Typically the superelastic metal tube 101 has an outer diameter of about 0.4 to 1.0 mm, preferably 0.5 to 0.8 mm, a wall thickness of about 50 to 200 mm, preferably 80 to 150 μm, a length of about 500 to 4,000 mm, preferably 1,000 to 3,000 mm, a buckling strength (yield stress under load) of about 5 to 200 kg/mm$^2$, preferably 8 to 150 kg/mm$^2$ at 22° C., and a restoring stress (yield stress upon unloading) of about 3 to 180 kg/mm$^2$, preferably 5 to 130 kg/mm$^2$ at 22° C.

Figure 26:
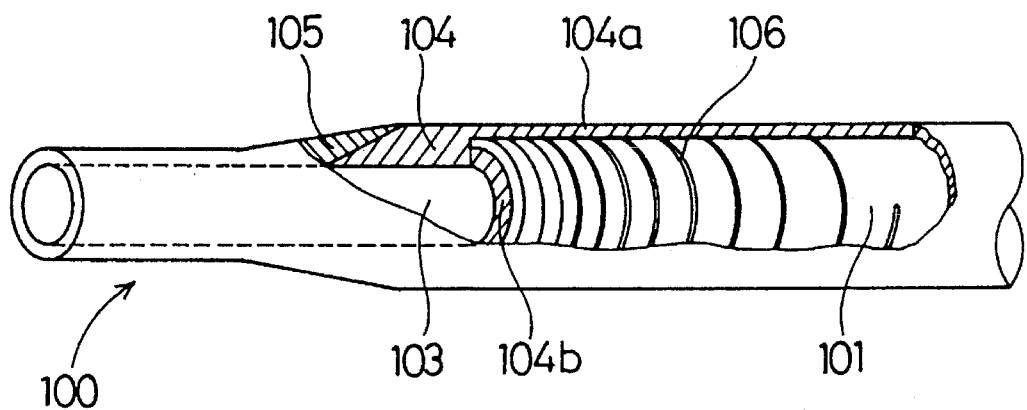
FIG. 26 is a partially cut-away perspective view of the distal portion of the catheter shown in FIG. 24.

In the catheter 100 of this embodiment, the superelastic metal tube 101 has a distal zone 102c where a spiral slit 106 is formed as shown in FIG. 25 and FIG. 26 which is an enlarged partially cut-away view of the distal zone in FIG. 25. The slit width is not fixed since it is determined in consideration of the catheter outer diameter or the like. The slit width is preferably 0.1 to 1.5 mm, more preferably 0.5 to 1.0 mm. In other words, the slit width is preferably about ⅙ to ⅔, more preferably ⅓ to ¼ of the outer diameter of the metal tube. Within this range, the metal tube distal zone is fully flexible and not broken during operation. Where the spiral slit 106 has a constant pitch, the pitch is preferably about 0.5 to 2.0 mm, more preferably 0.5 to 1.0 mm because within this range, the metal tube distal zone is fully flexible and not broken during operation. The extent of the distal portion of the metal tube where the slit is formed is determined by taking into account the length of the catheter or the like. Typically the slit is formed in a distal region of the metal tube which extends about 100–1,000 mm, preferably 150–500 mm from the distal edge thereof.

In one preferred example, the spiral slit 106 is formed at increasing pitches. As shown in FIGS. 25 and 26, the slit pitch is shorter at the distal end (left-hand side) and longer on the proximal end (right-hand side) of the distal zone 102c. Then the superelastic metal tube 101 becomes more flexible toward the distal end. Such a gradual change of physical properties ensures smoother bending of the metal tube distal zone and easier manipulation of the catheter. Where the slit has a variable pitch, the pitch is preferably about 0.5 to 3.0 mm at the distal end and about 5 to 10 mm at the proximal end of the distal zone 102c, and an intermediate value at an intermediate region. It is also acceptable that the pitch be continuously increased from the distal end toward the proximal end. Within this range, the metal tube distal zone is fully flexible and not broken during operation.

A single spiral slit is formed in the embodiment of FIGS. 25 and 26 although two or more slits may be formed.

The superelastic metal tube 101 is covered with the synthetic resin layer 104. More particularly, the synthetic resin layer 104 covering the metal tube 101 includes outside and inside layers 104a and 104b covering the outside and inside surfaces of the metal tube 101, respectively. Past the distal end of the metal tube 101, the outside and inside resin layers 104a and 104b merge into an integral layer. It is only required that the resin layer covers at least the outside surface of the metal tube while the inside resin layer 104b may be omitted.

Although part of the resin material of which the resin layer is made may flow into the slits 106 in the superelastic metal tube 101, it is preferred that the slits be substantially free of the resin material and empty. In the absence of the resin material flowing into the slits 106, flexural motion of the metal tube 101 is never obstructed.

In the catheter 100 of this embodiment, the distal section 102a is the tip member 105 made of synthetic resin which is fixedly connected to the distal end of the main body section 102b or integrated resin layer 104. In the illustrated embodiment, the synthetic resin layer 104 is tapered forward while the base portion of the tip member 105 is also tapered in conformity with the tapered layer 104. The distal end 109 of the tip member 105 and hence the catheter 100 has a smaller diameter than the remainder. It is preferred that the leading edge 109 of the tip member 105 and hence the catheter 100 presents a blunt curved surface for preventing damage to the vascular wall and improving manipulation of the catheter.

Instead of the tip member 105, the synthetic resin layer 104 covering the metal tube 101 may be extended forward (leftward in FIG. 25) to form the distal section 102a integral with the resin layer 104.

Synthetic resins are used to form the synthetic resin layer 104 and tip member 105. Examples include thermoplastic resins such as polyolefins (e.g., polyethylene and polypropylene), polyolefin elastomers (e.g., ethylene elastomers, polypropylene elastomers, and ethylene-propylene copolymer elastomers), polyvinyl chloride, ethylene-vinyl acetate copolymers, polyamide elastomers, and polyurethane, and fluoro-resins, and silicone rubber. Preferred are the polyethylene, polyamide elastomers, and polyurethane. Particularly when the catheter is applied to a catheter for administering an embolic substance (e.g., a dimethyl sulfoxide solution of cyanoacrylate or ethylene-vinyl alcohol copolymers) into a cerebral blood vessel, those synthetic materials which are insoluble in such solvents as dimethyl sulfoxide are preferred. Preferred synthetic resins for such catheters are solvent-resistant resins such as polyamide elastomers.

The synthetic resin layer 104 should preferably be flexible enough not to obstruct bending of the superelastic metal tube 101. It is also preferred to incorporate into the synthetic resin of the layer 104 and tip member 105 a radiopaque contrast substance in powder form, for example, elemental metals such as barium, tungsten and bismuth and compounds thereof. This facilitates the operator to locate the catheter over its entirety during insertion into a blood vessel. Preferably the synthetic resin layers 104a and 104b covering the metal tube each have a thickness of about 5 to 300 μm, more preferably 10 to 200 μm.

Typically, the main body section 102b of the catheter has an outer diameter of about 0.9 to 7.0 mm, preferably 1.0 to 6.0 mm. The distal section 102a has an outer diameter of about 0.4 to 1.0 mm, preferably 0.5 to 0.8 mm.

The outside surface of the catheter (more specifically, the outside surface of outside resin layer 104a) may be coated with a biocompatible, especially anti-thrombotic, resin. Preferred anti-thrombotic resins are poly(hydroxyethyl methacrylate) and hydroxyethyl methacrylate-styrene copolymers (e.g., HEMA-St-HEMA block copolymers). Especially when a radiopaque contrast substance is mixed with a synthetic resin, such coating is preferred for eliminating the surface roughness associated with the radiopaque powder. While biocompatible resins are preferred, the same synthetic resin as used in forming the layer or tip member, but free of radiopaque powder may be thinly coated.

Also the catheter (outside resin layer 104a) on its outside surface is preferably treated so that the surface may exhibit lubricity when contacted with blood or body fluid. Such treatments include coating and fixation of hydrophilic polymers such as poly(2-hydroxyethyl methacrylate), poly(hydroxyethyl acrylate), hydroxypropyl cellulose, methyl vinyl ether-maleic anhydride copolymers, polyethylene glycol, polyacrylamide, and polyvinyl pyrrolidone.

To the catheter 100 at the proximal end (right end in FIG. 25) is fixedly mounted a hub 120. More particularly, a reinforcing sleeve 108 is fitted over the proximal end of the main body section 102b. The reinforcing sleeve 108 and the main body section 102b are inserted into a bore in the hub 120 and adhesively bonded thereto.

Figure 27:
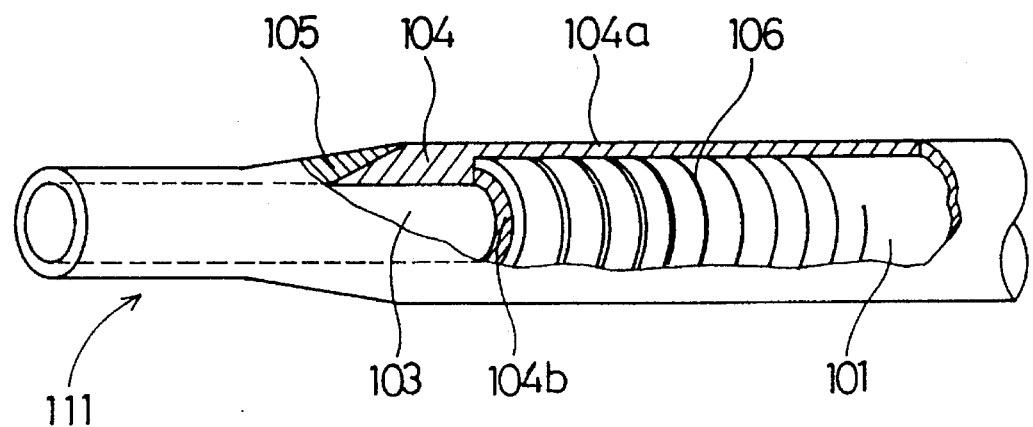
FIGS. 27, 28, 29, and 30 are partially cut-away perspective views of modified distal portions of the catheter.

The shape of slit is not limited to that shown in FIG. 26. FIG. 27 shows another example of the slit.

The catheter 111 of this embodiment has the same basic construction as the embodiment of FIGS. 25 and 26. In the catheter 111, the superelastic metal tube 101 is provided with a spiral slit 106 having a width which is greater at the distal end and smaller at the proximal end of the flexible zone. The slit width is reduced from the distal end toward the proximal end. Then the metal tube becomes more flexible toward the distal end, ensuring smoother bending of the metal tube distal zone and more effective manipulation of the catheter.

Although the slit width is determined in consideration of the catheter outer diameter or the like, it is preferably about 0.1 to 2.0 mm at the distal end and about 0.1 to 0.5 mm at the proximal end. In other words, the slit width is preferably about ⅙ to ⅔, more preferably about ⅓ to ¼ of the outer diameter of the metal tube. Within this range, the metal tube distal zone is fully flexible and not broken during operation. In an intermediate region between the distal and proximal ends, the slit width may have an intermediate value or be gradually decreased from the distal end to the proximal end of the metal tube distal zone. The pitch of the slit 106 may be fixed or decreased continuously or stepwise from the distal end toward the proximal end. The extent of the distal zone of the metal tube where the slit is formed is determined by taking into account the length of the catheter or the like. Typically the slit is formed in a distal region of the metal tube which extends about 100–1,000 mm, preferably 150–500 mm from the distal edge thereof. A single spiral slit is formed in the embodiment of FIG. 27 although two or more slits may be formed.

Figure 28:
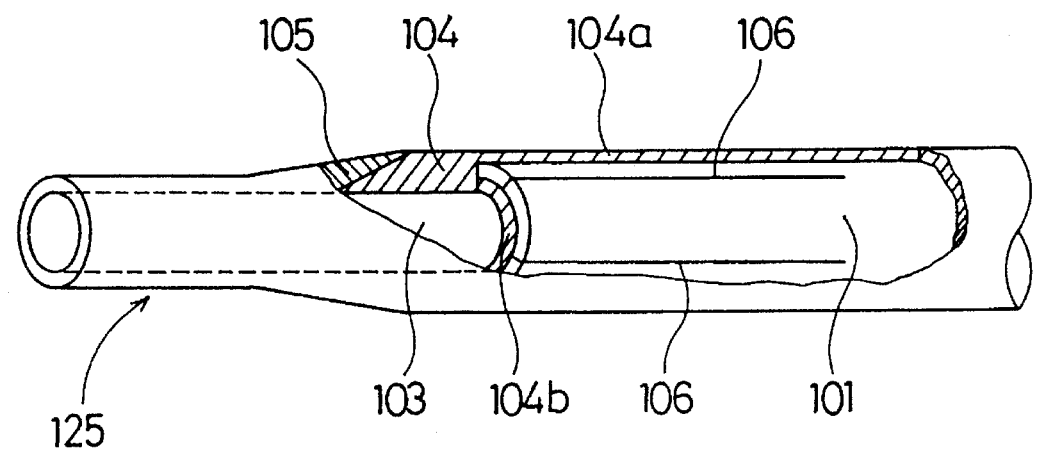

FIG. 28 shows a further example of the slit. The catheter 125 of this embodiment has the same basic construction as the embodiment of FIGS. 25 and 26. In the catheter 125, the superelastic metal tube 101 is provided with a plurality of equally spaced linear slits 106 extending parallel to the tube axis. The slits 106 render the distal zone of the metal tube flexible, ensuring smoother bending of the metal tube distal zone and easier manipulation of the catheter.

The slit width is not fixed since it is determined in accordance with the catheter outer diameter or the like. The slits preferably have a circumferential width of about 0.1 to 0.5 mm. Two to twelve slits 106 are preferably formed because within this range, the distal zone of the metal tube is fully flexible and not broken during operation. The slits preferably have a length of about 100 to about 1,000 mm, more preferably 150 to 500 mm.

Figure 29:
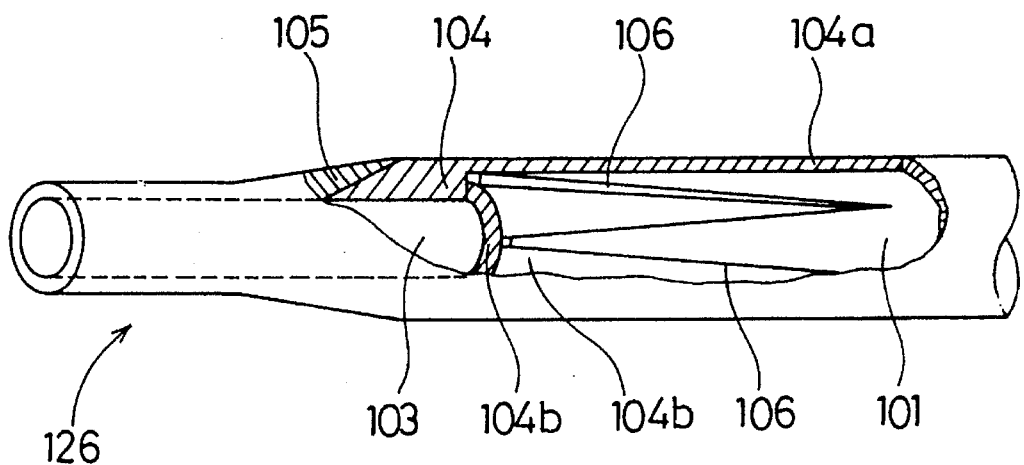

FIG. 29 shows a further example of the slit. The catheter 126 of this embodiment has the same basic construction as the embodiment of FIGS. 25 and 26. In the catheter 126, the superelastic metal tube 101 is provided with a plurality of triangular slits 106 extending from the distal end to the proximal end of the distal zone 102c. The provision of slits 106 makes the distal zone of the metal tube more flexible than the remainder. As shown in FIG. 29, the slits 106 are gradually decreased in width from the distal end to the proximal end of the distal zone of the superelastic metal tube 101, or differently stated, gradually increased in width toward the distal end. The slit has the maximum width at the distal end of the metal tube 101. Then as one goes toward the distal end, the superelastic metal tube 101 is more flexible and deformable and the side wall is more deformable radially inward and outward. Preferably two to eight slits 106 are formed at approximately equal intervals. Also preferably, the slits 106 have a maximum width of about 0.05 to 0.5 mm at the distal end and a length of about 100 to 1,000 mm, more preferably 150 to 500 mm.

Figure 30:
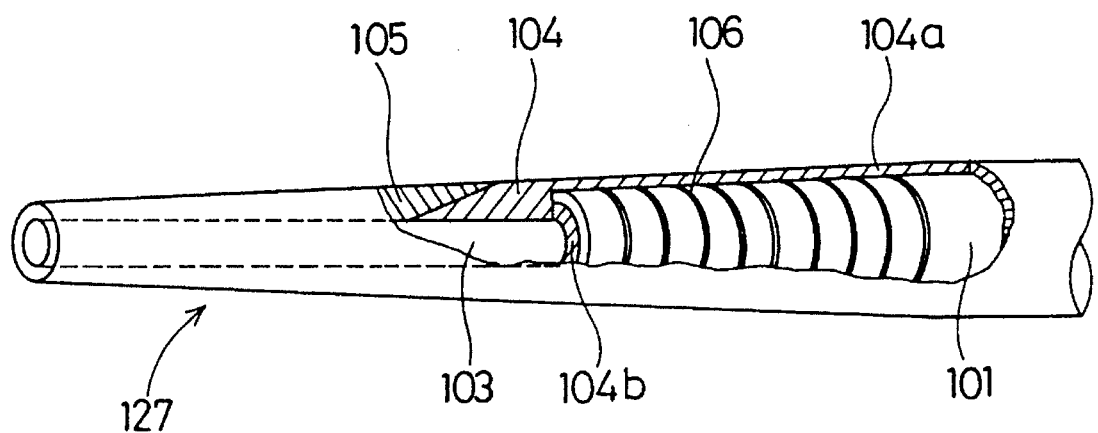

A still further example of the superelastic metal tube and slit is illustrated in FIG. 30.

In the catheter 127 of this embodiment shown in FIG. 30, the superelastic metal tube 101 includes a distal portion which is tapered or diametrically reduced toward the distal end (left-hand end in FIG. 30). A spiral slit 106 is formed in the tapered distal zone of the metal tube 101. Such a tube can be prepared by forming a tube having a tapered end portion and machining a spiral slit in the tapered portion. The tube having a tapered end portion can also be prepared by machining a spiral slit in one end portion of a metal tube of a fixed diameter and axially stretching the slit portion.

The slit width is not fixed since it is determined in accordance with the catheter outer diameter or the like. The slit width is preferably about 0.1 to 1.5 mm, more preferably 0.5 to 1.0 mm. Where the spiral slit 106 has a constant pitch, the pitch is preferably about 0.5 to 2.0 mm, more preferably 0.5 to 1.0 mm. The extent of the distal portion of the metal tube where the slit is formed is determined by taking into account the length of the catheter or the like. Typically the slit is formed in a distal region of the metal tube which extends about 100–1,000 mm, preferably 150–500 mm from the distal edge thereof.

Also preferably, the spiral slit 106 has a reduced pitch at the distal end and an increased pitch at the proximal end of the metal tube distal zone. Where the slit has a variable pitch, the pitch is preferably about 0.5 to 3.0 mm at the distal end and about 5 to 10 mm at the proximal end of the distal zone and an intermediate value at an intermediate region. It is also acceptable that the pitch be continuously increased from the distal end toward the proximal end. A single spiral slit is formed in the embodiment of FIG. 30 although two or more slits may be formed.

Figure 31:
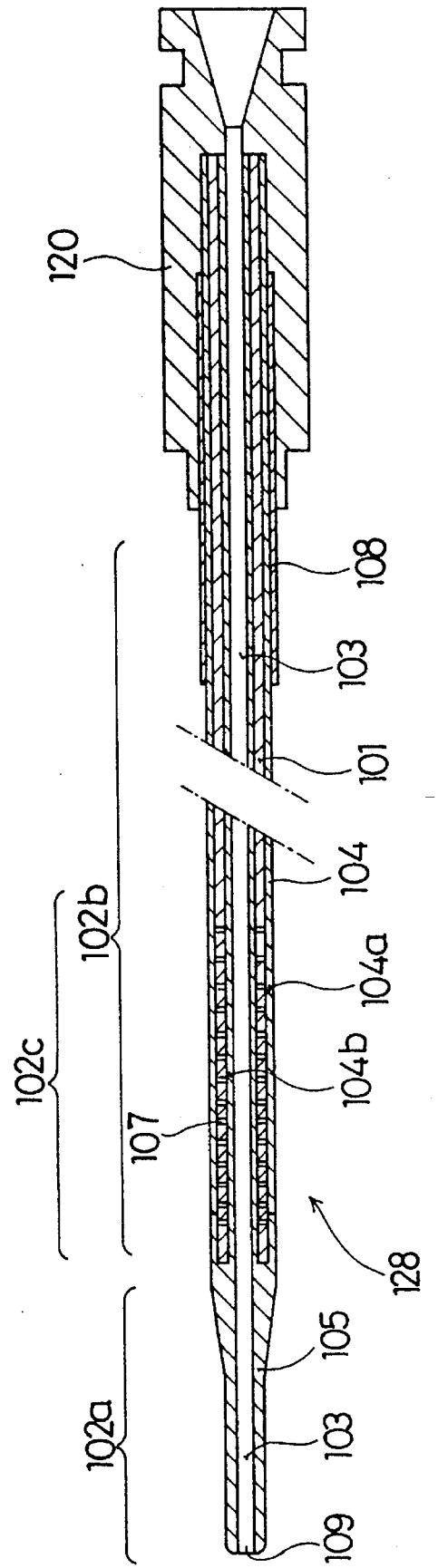
FIG. 31 is an overall, partially omitted, cross-sectional view of a catheter according to a still further embodiment of the invention.
Figure 32:
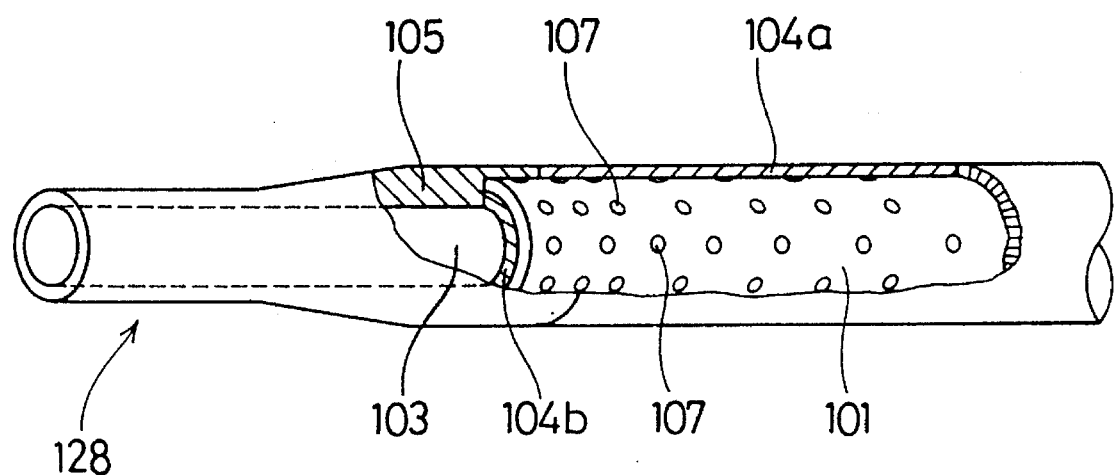
FIG. 32 is a partially cut-away perspective view of the distal portion of the catheter shown in FIG. 31.

Referring to FIGS. 31 and 32, there is illustrated a catheter according to a further embodiment of the invention.

The catheter 128 of the illustrated embodiment has the same basic construction as that shown in FIGS. 24 to 26 and like parts are designated by the same numerals. The difference of the catheter 128 of this embodiment from the catheter 100 of the previous embodiment resides in the construction of the superelastic metal tube 101 and tip member 105. In the catheter 128, the synthetic resin layer 104a covering the superelastic metal tube 101 terminates at a position retracted a distance from the distal end of the metal tube toward the proximal end, that is, the distal end of the metal tube 101 is not covered with the resin. Instead, the tip member 105 defines an extra cylindrical rear bore into which is inserted the exposed distal portion of the metal tube 101. The tip member 105 and the synthetic resin layer 104 are joined together with the distal portion of the metal tube 101 inserted into the cylindrical bore of the tip member 105.

The superelastic metal tube 101 in a distal zone is provided with a plurality of perforations 107 so that the metal tube distal zone is more flexible and bendable than the remainder. The flexible distal zone of the metal tube 101 reduces the difference in physical properties between the metal tube 2b and the resin layer 104 and tip member 105, thereby preventing separation and differential motion therebetween and facilitating manipulation of the catheter.

The diameter of perforations is not fixed since it is determined in accordance with the number of perforations, the outer diameter of metal tube and the like. Typically the perforations 107 have a diameter of about 0.1 to 0.4 mm, preferably 0.2 to 0.3 mm. In other words, the pore diameter is preferably about $1/10$ to $1/3$ of the outer diameter of the metal tube. Within this range, the metal tube distal zone is fully flexible and not broken during operation. The perforations 107 are preferably spaced a distance of about 0.1 to 0.5 mm. Within this range, the metal tube distal zone is fully flexible and not broken during operation. The extent of the distal zone of the metal tube which is perforated is determined by taking into account the catheter length or the like. Typically the perforations are formed in a distal region of the metal tube which extends about 100–1,000 mm, preferably 150–500 mm from the distal edge thereof.

As shown in FIGS. 31 and 32, more perforations 107 are distributed near the distal end than near the proximal end of the perforated zone. Then the superelastic metal tube 101 becomes more flexible toward the distal end. Such a gradual change of physical properties ensures smoother bending of the metal tube distal zone and more adequate manipulation of the catheter. More specifically, the number of perforations 107 is gradually increased from the proximal end to the distal end of the perforated zone as shown in FIGS. 31 and 32. Then the superelastic metal tube 101 becomes more flexible toward the distal end, ensuring smoother bending of the metal tube distal zone and more convenient manipulation of the catheter. Where the perforation distribution is varied in this way, the spacing between perforations is about 0.1 to 0.2 mm at the distal end and about 0.3 to 0.5 mm at the proximal end. In an intermediate region between the distal and proximal ends, the spacing between perforations has an intermediate value or is gradually varied.

Instead of the varying perforation distribution, the diameter or area of perforations may be varied such that the diameter or area is greater near the distal end than near the proximal end.

With respect to the shape, the perforations need not be true circle and may be ellipsoidal, for example, oval holes elongated in a circumferential or axial direction of the metal tube or polygonal such as square or pentagonal holes. Each perforation preferably has an area of 0.007 to 0.13 $mm^2$.

Although part of the synthetic resin material of which the resin layer 104 and tip member 105 are made may flow into the holes 107 in the superelastic metal tube 101, it is preferred that the holes 107 be substantially free of the resin material and empty. In the absence of the resin material flowing into the holes, the metal tube 101 undergoes free flexural motion.

Slits or holes are formed in the superelastic metal tube by any of conventional techniques including laser machining (e.g., YAG laser), electric discharge machining, chemical etching, machining, and combinations thereof.

EXAMPLE

Examples of the catheter according to the invention are given below by way of illustration and not by way of limitation.

A catheter as shown in FIGS. 24 and 25 was fabricated. A pipe of Ti—Ni alloy containing 51 atom % of nickel was cold worked into a superelastic metal tube having an outer diameter of 1.0 mm, an inner diameter of 0.85 mm, and a length of 100 cm. A spiral slit was cut in a distal zone of the metal tube which extended 20 cm from the distal end, using a YAG laser machine model ML-4140A (Miyachi Technos K.K., laser irradiation at a power of 4 W and an irradiation rate of 10 mm/min.). The spiral slit had a constant width of 0.5 mm and a pitch which gradually increased from 1 mm at the distal end to 10 mm at the terminus. The metal tube including the slit portion was covered on both the inside and outside surfaces with polyethylene. The polyethylene coating did not substantially flow into the slit and the slit remained empty. The resin coated superelastic metal tube constituted a catheter main body section. The resin layer covering the metal tube was 0.04 mm thick on the outside and 0.03 mm on the inside. The catheter main body section was 1.08 mm in outer diameter and 0.79 mm in inner diameter.

A tip member constituting a catheter distal section was molded from polyethylene to a length of 20 cm, an outer diameter of 0.9 mm and an inner diameter of 0.8 mm. The tip member was connected to the distal end of the resin-coated superelastic metal tube by fusion welding.

A hub as shown in FIG. 25 was molded from polycarbonate and adhesively joined to the proximal end of the resin-coated superelastic metal tube, completing the catheter.

Figure 33:
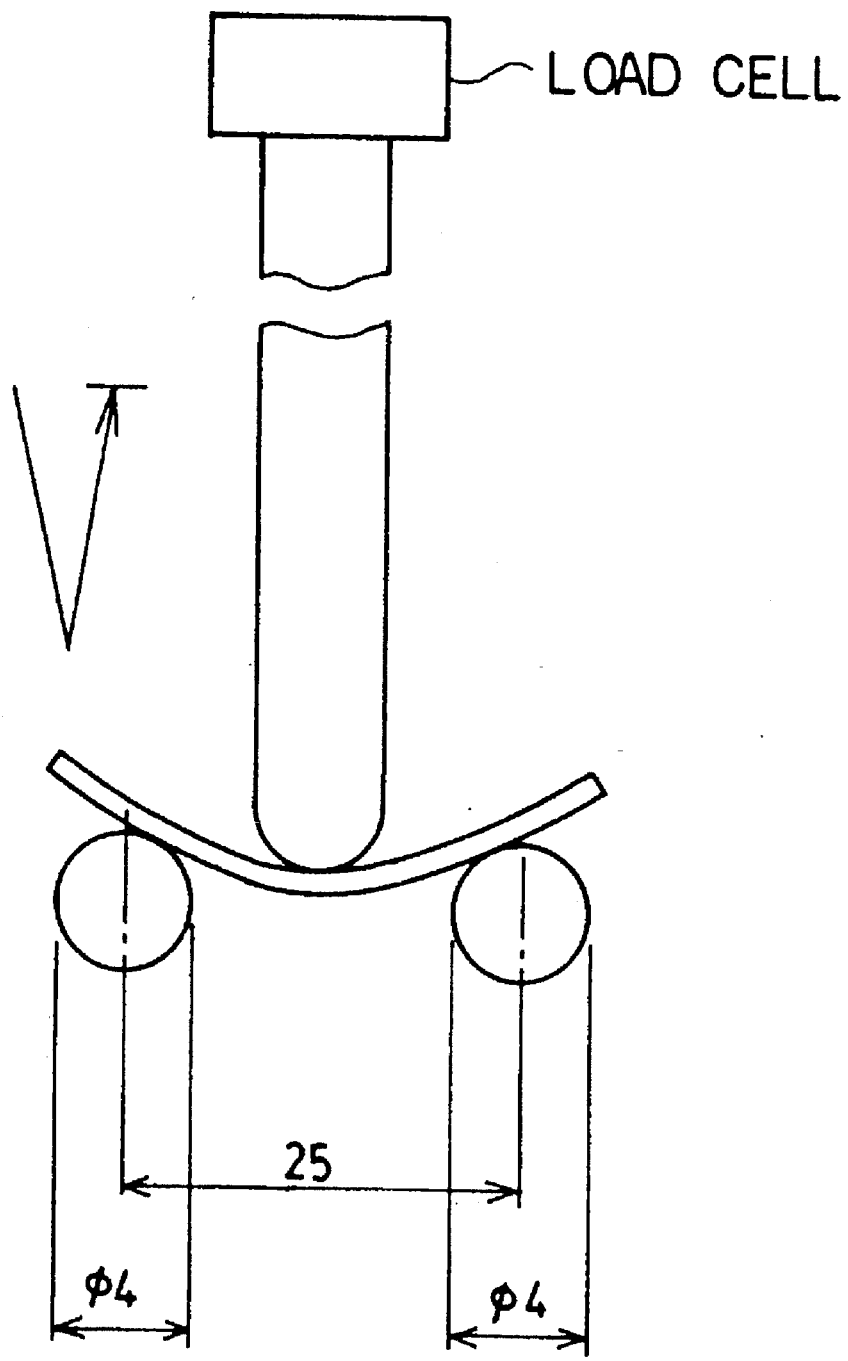
FIG. 33 illustrates how to measure the modulus of elasticity of a catheter.

The catheter was measured for modulus of elasticity at different positions. For measurement, Autograph AGS-100D manufactured by Shimazu Mfg. K.K. was used. Measurement was done as shown in FIG. 33 by setting a pair of rods having a diameter of 4 mm at a center-to-center distance of 25 mm, resting a selected area of the catheter on the rods, and loading the span portion by means of a pusher having a semispherical lower end.

Test conditions are shown below.

Test mode: cycle (down start)
Load cell: 5000 gf
F.S. load: 2500 gf (x2)
Test speed: 5 mm/min.
Minimum stroke: 0.00 mm stop
Maximum stroke: 2.00 mm return
Chart control: X-P C (x50)

The results of measurements are shown in Table 1.

TABLE 1

| Catheter | Load |
| --- | --- |
| Main body section, no slit area | 274 g |
| Main body section, slit, 10 mm pitch area | 135 g |
| Main body section, slit, 5 mm pitch area | 79 g |
| Main body section, slit, 2 mm pitch area | 26 g |
| Distal section (solely polyethylene) | 14 g |

As is evident from Table 1, the catheter of the invention has a gradual change in physical property from the main body portion of the metal tube to the most distal end of the catheter through the metal tube distal zone. There has been described a vascular dilatation instrument having a fully flexible distal zone and capable of transmitting translational and torsional forces from the proximal end to the distal end of the instrument (improved in pushability and torque transmission). The distal zone of the superelastic metal tube is more flexible and deformable than the main body portion. The flexible distal zone of the metal tube provides a smooth transition from the main body portion to the leading resinous portion. When a load is applied to the transition between the relatively stiff main body portion and the relatively flexible distal portion, the distal portion follows the load and deforms in the loading direction. This prevents angular folding at the transition which would otherwise occur due to the difference in physical properties between the metal tube and the synthetic resin.

The same applies to the catheter.

When a spiral slit or perforations are formed in the distal zone of the metal tube, the distal zone becomes more flexible and bendable. This minimizes the difference in physical properties between the metal tube and the synthetic resin layer, eliminating separation and differential motion therebetween. The instrument or catheter is thus more smooth and effective to manipulate.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A vascular dilatation instrument comprising:
    an inner tube defining a first lumen extending between an open distal end and a proximal portion,
    an outer tube disposed coaxially around said inner tube, having a distal end retracted a predetermined distance from the distal end of said inner tube and a proximal portion, and defining a second lumen with the outside surface of said inner tube,
    an inflatable member having one end attached to said inner tube and another end attached to said outer tube, and defining an interior space in fluid communication with said second lumen,
    a first opening disposed in the proximal portion of said inner tube in communication with said first lumen, and
    a second opening disposed in the proximal portion of said outer tube in fluid communication with said second lumen,
    wherein
    at least one of said inner tube and said outer tube includes a main body section based on a superelastic metal tube and a distal section made of a synthetic resin, the superelastic metal tube including a deformable distal zone which is more flexible than the remainder of the metal tube, and the deformable distal zone of said superelastic metal tube is gradually increased in flexibility from the proximal end to the distal end of the zone.

2. A vascular dilatation instrument according to claim 1 wherein said outer tube includes the superelastic metal tube and a synthetic resin tube covering the surface of said metal tube, said synthetic resin tube protruding beyond the distal end of said metal tube to form the distal section of said outer tube.

3. A vascular dilatation instrument according to claim 1 wherein said inner tube includes the superelastic metal tube and a synthetic resin tube covering the surface of said superelastic metal tube, said synthetic resin tube protruding beyond the distal end of said superelastic metal tube to form the distal section of said inner tube.

4. A vascular dilatation instrument according to claim 1 wherein said superelastic metal tube is provided with a slit extending from the distal end toward the proximal end.

5. A vascular dilatation instrument according to claim 1 wherein said superelastic metal tube is provided with a plurality of perforations in the distal zone thereof.

6. A vascular dilatation instrument according to claim 4 wherein said slit is a spiral slit.

7. A vascular dilatation instrument according to claim 6 wherein the width of said spiral slit in an intermediate region between the distal and proximal ends of said deformable distal zone is an intermediate value between a distal end and proximal ends of said deformable distal zone.

8. A vascular dilatation instrument according to claim 6 wherein the pitch of said slit is decreased stepwise from a distal end of said deformable distal zone toward a proximal end of said deformable distal zone.

9. A vascular dilatation instrument according to claim 6 wherein said spiral slit is gradually reduced in pitch toward the distal end of said metal tube.

10. A vascular dilatation instrument according to claim 6 wherein said spiral slit is gradually increased in width toward the distal end of said metal tube.

11. A vascular dilatation instrument comprising:
a tubular member having a lumen therethrough and an opening in fluid communication with said lumen,
a leading head, and
an inflatable member having one end attached to said tubular member and another end attached to said leading head and defining an interior space in fluid communication with said lumen through said opening,
said tubular member including a main body portion based on a superelastic metal tube and a distal portion made of a synthetic resin, the superelastic metal tube including a deformable distal zone which is more flexible than the remainder of the metal tube, and the deformable distal zone of said superelastic metal tube is gradually increased in flexibility from the proximal end to the distal end of the zone.

12. A vascular dilatation instrument according to claim 11 further comprising an elastic shaft extending through said lumen and having a distal end connected to said leading head.

13. A vascular dilatation instrument according to claim 11 wherein said tubular member includes the superelastic metal tube and a synthetic resin tube covering the surface of said metal tube, said synthetic resin tube protruding beyond the distal end of said metal tube to form the distal portion of said tubular member.

14. A vascular dilatation instrument according to claim 11 wherein said superelastic metal tube is provided with a slit extending from the distal end toward the proximal end thereof.

15. A vascular dilatation instrument according to claim 11 wherein said superelastic metal tube is provided with a plurality of perforations in the distal zone thereof.

16. A vascular dilatation instrument according to claim 11 wherein the deformable distal zone of said superelastic metal tube is more flexible at the distal end than at the proximal end of the zone.

17. A vascular dilatation instrument according to claim 14 wherein said slit is a spiral slit.

18. A vascular dilatation instrument according to claim 17 wherein the width of said spiral slit in an intermediate region between the distal and proximal ends of said deformable distal zone is an intermediate value between a distal end and proximal ends of said deformable distal zone.

19. A vascular dilatation instrument according to claim 17 wherein the pitch of said slit is decreased stepwise from a distal end of said deformable distal zone toward a proximal end of said deformable distal zone.

20. A vascular dilatation instrument according to claim 17 wherein said spiral slit is gradually reduced in pitch toward the distal end of said metal tube.

21. A vascular dilatation instrument according to claim 17 wherein said spiral slit is gradually increased in width toward the distal end of said metal tube.

22. A catheter comprising:
a main body section including a superelastic metal tube and a synthetic resin layer covering said metal tube, and
a distal section made of a synthetic resin,
the superelastic metal tube including a deformable distal zone which is more flexible than the remainder of the metal tube, and the deformable distal zone of said superelastic metal tube is gradually increased in flexibility from the proximal end to the distal end of the zone.

23. A catheter according to claim 22 wherein said superelastic metal tube is provided with a slit extending from the distal end toward the proximal end thereof.

24. A catheter according to claim 23 wherein said slit is a spiral slit.

25. A catheter according to claim 24 wherein the width of said spiral slit in an intermediate region between the distal and proximal ends of said deformable distal zone is an intermediate value between a distal end and proximal ends of said deformable distal zone.

26. A catheter according to claim 24 wherein the pitch of said slit is decreased stepwise from a distal end of said deformable distal zone toward a proximal end of said deformable distal zone.

27. A catheter according to claim 24 wherein said spiral slit is gradually reduced in pitch toward the distal end of said metal tube.

28. A catheter according to claim 24 wherein said spiral slit is gradually increased in width toward the distal end of said metal tube.

29. A catheter according to claim 22 wherein said superelastic metal tube is provided with a plurality of perforations in the distal zone thereof.

30. A catheter according to claim 22 wherein the deformable distal zone of said superelastic metal tube is more flexible at the distal end than at the proximal end of the zone.

31. A vascular dilatation instrument according to claim 1 wherein the deformable distal zone of said superelastic metal tube is more flexible at the distal end than at the proximal end of the zone.

* * * * *

UNITED STATES PATENT AND TRADEMARK OFFICE
CERTIFICATE OF CORRECTION

PATENT NO. : 5,507,766
DATED : April 16, 1996
INVENTOR(S) : Takahiro KUGO et al

It is certified that error appears in the above-indentified patent and that said Letters Patent is hereby corrected as shown below:

In Column 1, line 24, delete "time" and insert -- the --.

In Column 4, line 14, delete "superelasLic" and insert -- superelastic --.

In Column 11, line 46, delete "100-1,000 ms," and insert -- 100-1,000 mm, --.

In Column 24, line 8, delete "50 to 200 mm" and insert -- 50 to 200 $\mu$m --.

Signed and Sealed this

Eighth Day of October, 1996

Attest:

BRUCE LEHMAN

Attesting Officer

Commissioner of Patents and Trademarks